US008129197B2

(12) United States Patent
Báthori et al.

(10) Patent No.: US 8,129,197 B2
(45) Date of Patent: Mar. 6, 2012

(54) CHOLESTEROL LOADED INSECT CELL MEMBRANES AS TEST PROTEINS

(75) Inventors: György Báthori, Budapest (HU); Dóra Méhn, Szeged (HU); Pál Ákos, Zalaegerszeg (HU); Péter Krajcsi, Budapest (HU); Lajos Szente, Budapest (HU); Éva Fenyvesi, Budapest (HU); Ágnes Telbisz, Budapest (HU); Balázs Sarkadi, Budapest (HU); András Váradi, Budapest (HU); Szilvia Gedey, Szeged (HU); Hristos Glavinas, Szeged (HU); Emese Kis, Mezöberény (HU); Tünde Nagy, Pécs (HU); Attila Németh, Budapest (HU); Éva Molnár, Szeged (HU)

(73) Assignee: SOLVO Biotechnológial ZRT., Budaörs (HU)

( * ) Notice: Subject to any disclaimer, the term of this patent is extended or adjusted under 35 U.S.C. 154(b) by 224 days.

(21) Appl. No.: 12/300,479

(22) PCT Filed: May 14, 2007

(86) PCT No.: PCT/HU2007/000041
§ 371 (c)(1),
(2), (4) Date: Jan. 29, 2009

(87) PCT Pub. No.: WO2007/132279
PCT Pub. Date: Nov. 22, 2007

(65) Prior Publication Data
US 2010/0021927 A1 Jan. 28, 2010

(30) Foreign Application Priority Data
May 12, 2006 (HU) .................................. 0600408
Sep. 27, 2006 (HU) .................................. 0600754

(51) Int. Cl.
G01N 33/567 (2006.01)
G01N 33/53 (2006.01)
C12P 1/00 (2006.01)
C12P 21/06 (2006.01)
C12N 5/07 (2010.01)
C12N 5/00 (2006.01)

(52) U.S. Cl. .......... 436/503; 435/41; 435/7.8; 435/69.1; 435/348; 435/325

(58) Field of Classification Search ........................ None
See application file for complete search history.

(56) References Cited

U.S. PATENT DOCUMENTS
6,617,122 B1  9/2003  Hayden et al.
6,773,893 B1  8/2004  Tall
6,855,812 B2  2/2005  Hanscom et al.
2004/0096851 A1  5/2004  Wang et al.
2004/0175762 A1*  9/2004  Ozvegy et al. ................. 435/7.2
2004/0185456 A1  9/2004  Denefle et al.

FOREIGN PATENT DOCUMENTS
CN      1368551 A      9/2002
EP      1130400 A1     9/2001
HU      P0600754   *   9/2006
WO      0018912        4/2000
WO      0203066 A2     1/2002
WO      0210766 A2     2/2002
WO      0220527 A1     3/2002
WO      02071073 A2    9/2002
WO      03025174 A2    3/2003
WO      03035685 A1    5/2003
WO      2006005975 A2  1/2006

OTHER PUBLICATIONS

Contreras et al.: Combination of an enzymatic method and HPLC for the quantitation of cholesterol in cultured cells, The Journal of Lipid Research, (1992) 33, 931-936.
Dean et al.: The Human ATP-Binding Cassette (ABC) Transporter Superfamily, Genome Res. (2001) 11, 1156-1166.
Diop et al.: N-Linked glycosylation of the human ABC transporter ABCG2 on asparagine 596 is not essential for expression, transport activity, or trafficking to the plasma membrane, Biochemistry (2005) 44 5420-5429.
Feng et al.: ABCA1-mediated cholesterol efflux is defective in free cholesterol-loaded macrophages, J. Biol. Chem. (2002) 277(48) 43271-43280.
Garrigues et al.: The multidrug transporter, P-glycoprotein, actively mediates cholesterol redistribution in the cell membrane, Proc Natl Acad Sci U S A. (2002) 99: 10347-10352.
Gimpl et al.: Expression of the human oxytocin receptor in baculovirus-infected insect cells: high-affinity binding is induced by a cholesterol-cyclodextrin complex. Biochemistry (1995) 34: 13794-13801.
Gottesman et al.: Multidrug resistance in cancer: role of ATP-dependent transporters, Nat Rev Cancer (2002) 2 48-58.
Kamau et al.: Effect of the modulation of the membrane lipid composition on the localization and function of P-glycoprotein in MDR1-MDCK cells., In Vitro Cell Dev Biol Anim, (2005) 41: 207-216.
Keller et al.: Cholesterol Is Required for Surface Transport of Influenza Virus Hemagglutinin, J. Cell Biol. (1998) 140 (6) 1357-67.

(Continued)

Primary Examiner — Shulamith H Shafer
(74) Attorney, Agent, or Firm — Jason D. Voight

(57) ABSTRACT

The invention provides for a novel cholesterol loaded insect cell membrane preparation having an increased cholesterol level as compared to physiological cholesterol levels of insect cell membranes or to control insect cell membrane preparations without cholesterol loading, wherein said cholesterol loaded membrane preparation comprises an ABC transporter protein having an increased substrate transport activity due to increased cholesterol level of the membrane. The invention also relates to reagent kits comprising the preparations of the invention. The invention also relates to methods for manufacturing said preparations and methods for measuring any type of activity of the ABC transporters present in the cholesterol loaded membranes as well as studying or testing compounds and interaction of compounds and ABC transporters, in this assay systems. The invention also provides for a test system useful for testing whether ABC transporter proteins can be activated by cholesterol in an insect cell membrane.

21 Claims, 18 Drawing Sheets

OTHER PUBLICATIONS

Kopanchuk et al.: Changes in Membrane Fluidity During the Micelle Formation Determine the Efficiency of the Solubilization of Muscarinic Receptors, Proc Estonian Acad Sci Chem, (2001) 50(4), 229-240.

Le Goff et al.: Reevaluation of the role of the multidrug-resistant P-glycoprotein in cellular cholesterol homeostasis., J Lipid Res (2006) vol. 47, pp. 51-58.

Lockwich et al.: Assembly of Trp1 in a Signaling Complex Associated with Caveolin-Scaffolding Lipid Raft Domains, J. Biol. Chem. (2000), vol. 275(16), pp. 11934-11942.

Modok et al.: P-glycoprotein retains function when reconstituted into a sphingolipid- and cholesterol-rich environment, Journal of Lipid Research, (2004), vol. 45, pp. 1910-1918.

Mohrmann et al.: Absence of N-linked glycosylation does not affect plasma membrane localization of breast cancer resistance protein (BCRP/ABCG2), Cancer Chemother Pharmacol (2005), vol. 56, pp. 344-350.

Muller et al.: Altered drug-stimulated ATPase activity in mutants of the human multidrug resistance protein, J Biol Chem (1996), vol. 271, pp. 1877-1883.

Neubig et al.: International Union of Pharmacology Committee on Receptor Nomenclature and Drug Classification. XXXVIII. Update on terms and symbols in quantitative pharmacology. Pharmacol Rev (2003) vol. 55(4): pp. 597-606.

Noe et al.: Characterization of the Mouse Bile Salt Export Pump Overexpressed in the Baculovirus System; Hepatology, (2001), vol. 33(5), pp. 1223-1231.

Ozvegy et al.: Characterization of drug transport, ATP hydrolysis, and nucleotide trapping by the human ABCG2 multidrug transporter. Modulation of substrate specificity by a point mutation, J Biol Chem (2002) vol. 277(50), pp. 47980-47990.

Ozvegy-Laczka et al.: Single amino acid (482) variants of the ABCG2 multidrug transporter: major differences in transport capacity and substrate recognition, Biochim Biophys Acta (2005) vol. 1668, pp. 53-63.

Pál et al.: Cholesterol potentiates ABCG2 activity in a heterologous expression system—improved in vitro model to study function of human ABCG2, JPET (2007) vol. 321(3), pp. 1085.

Reinhard et al.: "Relations between the Physico-chemical Properties, the Chemical Reactivity and the Local-Anesthetic Activity" / Part 33: Studies on the interactions of the local-anesthetically active cinchocaine homologues with phospholipids, Arzneimittelforschung, (1975) vol. 25(9), pp. 1340-1351.

Sarkadi et al.: Expression of the human multidrug resistance cDNA in insect cells generates a high activity drug-stimulated membrane ATPase, J Biol Chem (1992) vol. 267(7), pp. 4854-4858.

Sarkadi et al.: Human multidrug resistance ABCB and ABCG transporters: participation in a chemoimmunity defense system, Physiol Rev 86 (2006) pp. 1179-1236.

Sheets et al.: Critical Role for Cholesterol in Lyn-mediated Tyrosine Phosphorylation of FceRl and Their Association with Detergent-resistant Membranes, J. Cell Biol. (1999) vol. 145(4): pp. 877-887.

Szakacs et al.: Targeting multidrug resistance in cancer, Nat Rev Drug Discov (2006) vol. 5, pp. 219-234.

Takahashi et al.: Purification and ATPase activity of human ABCA1., J. Biol. Chem. (2006) vol. 281(16), pp. 10760-10768.

Troost et al.: Modulation of cellular cholesterol alters P-glycoprotein activity in multidrug-resistant cells, Mol Pharmacol. (2004) vol. 66(5): pp. 1332-1339.

Vainio et al.: Dynamic association of human insulin receptor with lipid rafts in cells lacking caveolae, EMBO Rep. (2002) vol. 3(1), pp. 95-100.

Wrenn: Engineering Approaches to Cholesterol-Linked Diseases, Chemical Engineering, Summer, (2001) 1-25 http://www.gatewaytoalition.org/files/NewEh/htmls/wrenn.pdf.

Yunomae et al.: Involvement of cholesterol in the inhibitory effect of dimethyl-beta-cyclodextrin on P-glycoprotein glycoprotein and MRP2 function in Caco-2 cells., FEBS Lett. (2003) vol. 536(1-3): pp. 225-231.

Gimpl et al.: Human oxytocin receptors in cholesterol-rich vs. cholesterol-poor microdomains of the plasma membrane, Eur. J. Biochem., (2000) vol. 267, pp. 2483-2497.

Szakács et al.: Characterization of the ATPase cycle of human ABCA1: implications for its function as a regulator rather than an active transporter. Biochem. Biophys Res. Comm., (2001) vol. 288, pp. 1258-1264.

Janvilisri et al.: Sterol transport by the human breast cancer resistance protein (ABCG2) expressed in *Lactococcus lactis*. J. Biol, Chem. (2003) vol. 278, pp. 20645-20651.

Ishikawa et al.: Expression and functional characterization of human ABC transporter ABCG2 variants in insect cells., Drug Metab Pharmacokinet (2003) 18: 194-202.

Ozvegy et al.: Functional characterization of the human multidrug transporter, ABCG2, expressed in insect cells. Biochem Biophys Res Commun (2001) vol. 285: pp. 111-117.

* cited by examiner

Fig. 1
A
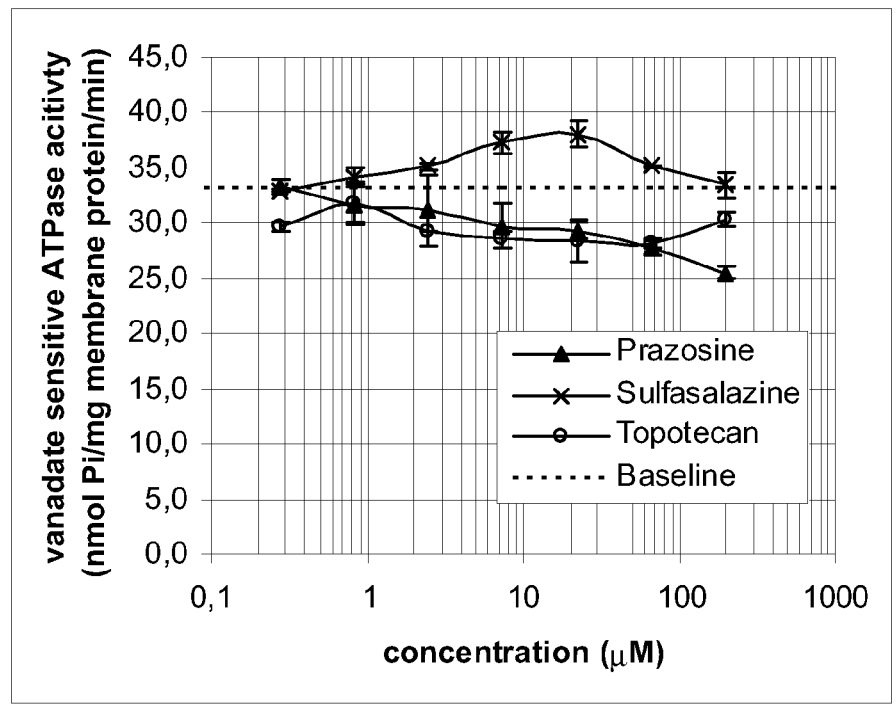
B
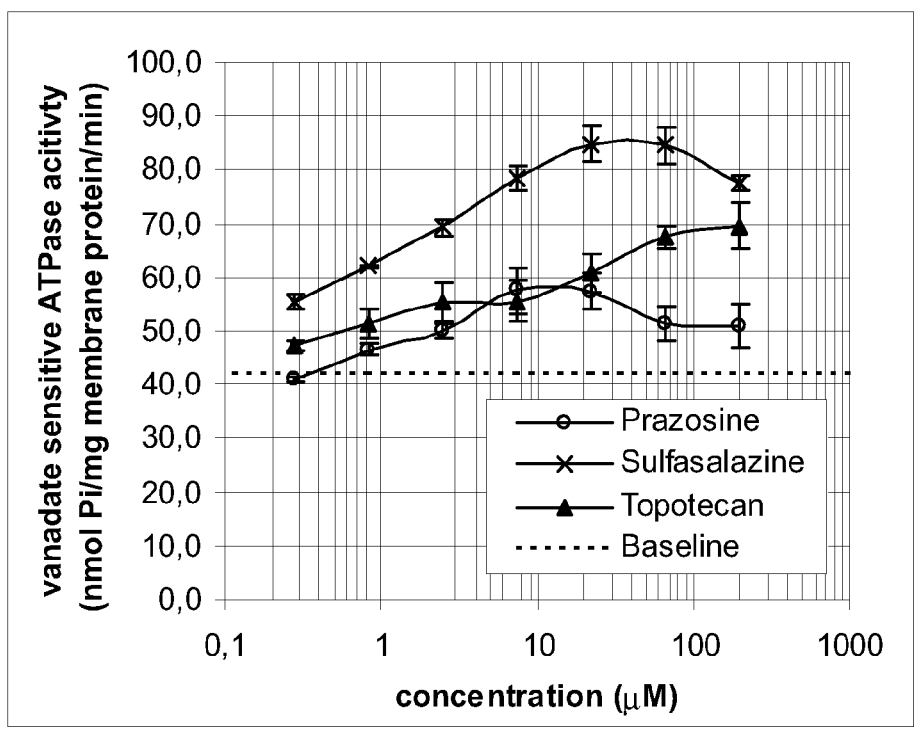

Fig. 2
A Effect of choleterol loading on membrane fractions isolated from BCRP transfected Sf9 cells
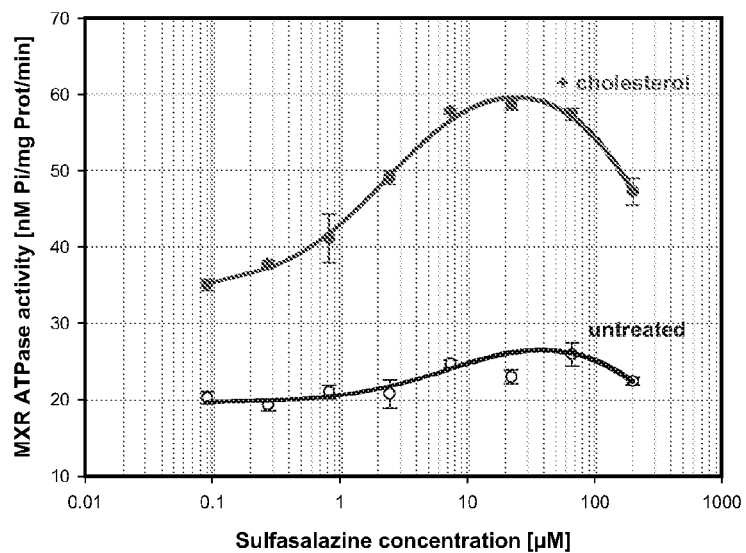
B Effect of cholesterol depletion on vesicles prepared from MXR-M cells
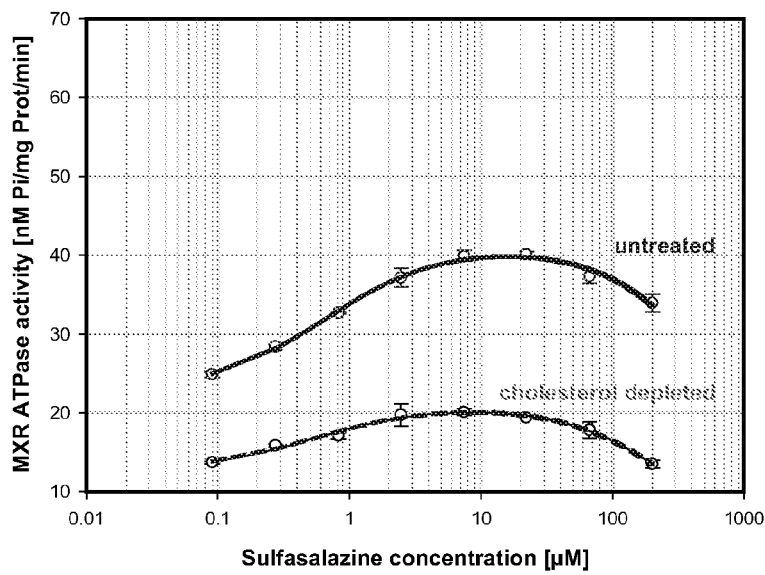

Fig. 3
A
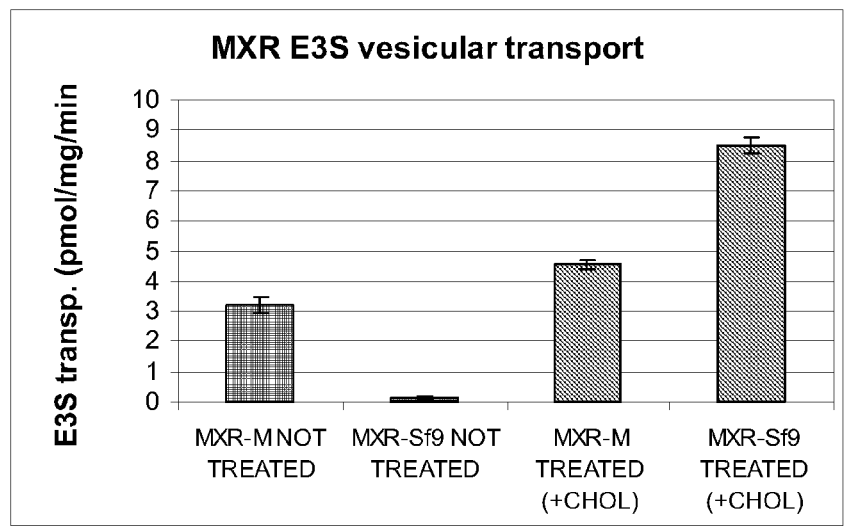
B
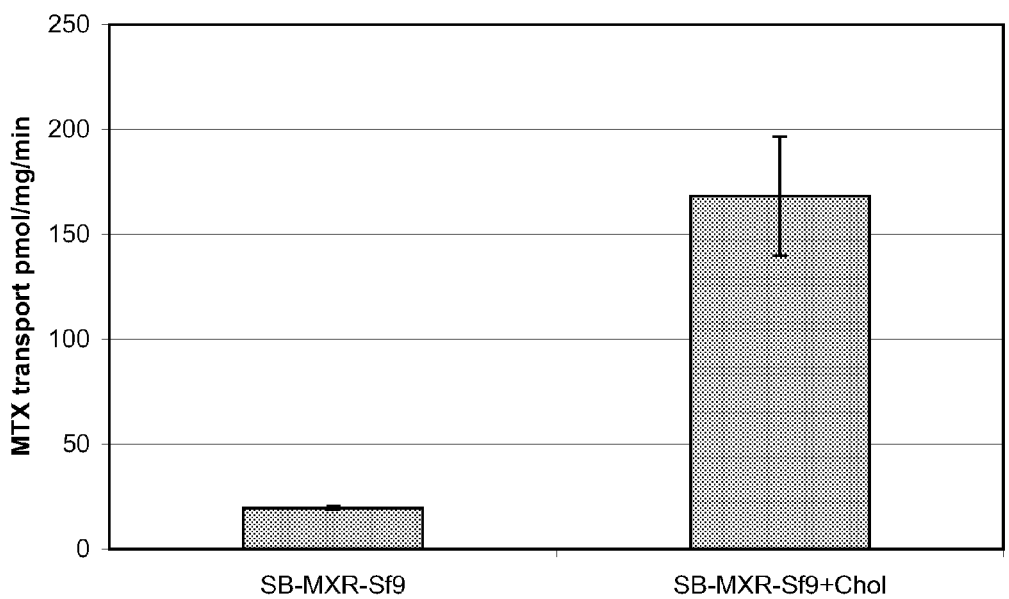

C

Fig. 4
4.A
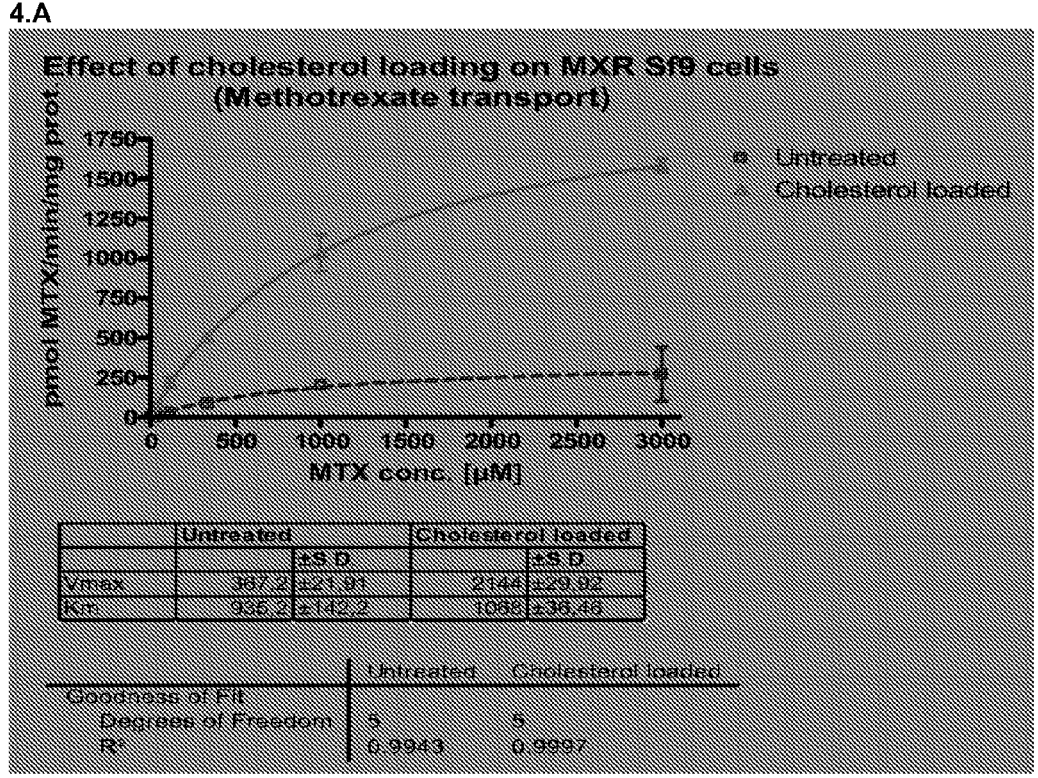
4.B
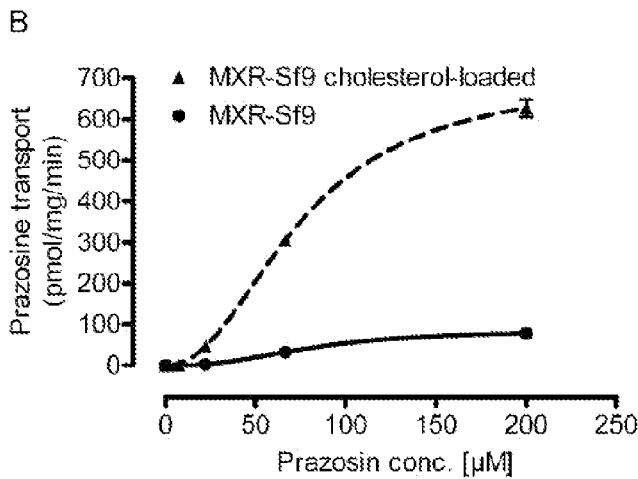

Fig. 8
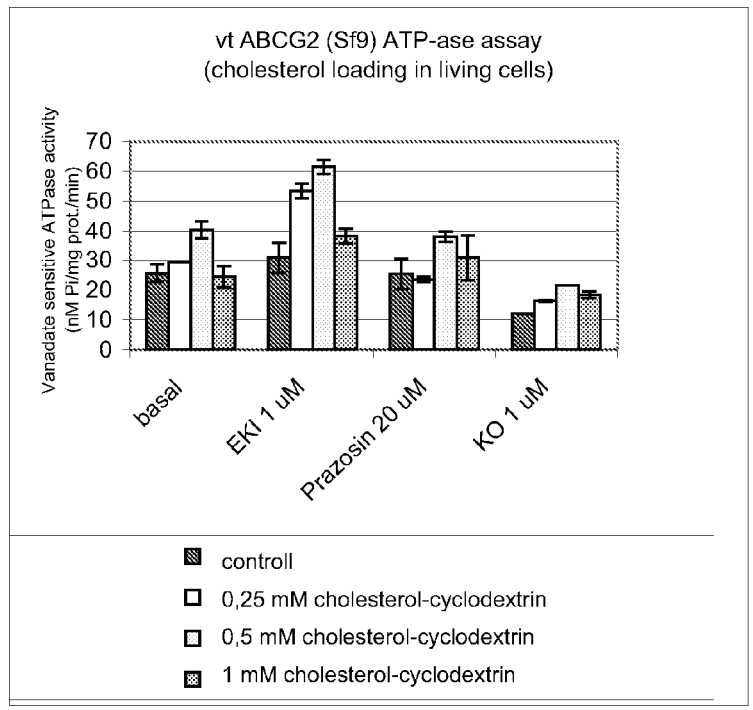
Fig. 9.a
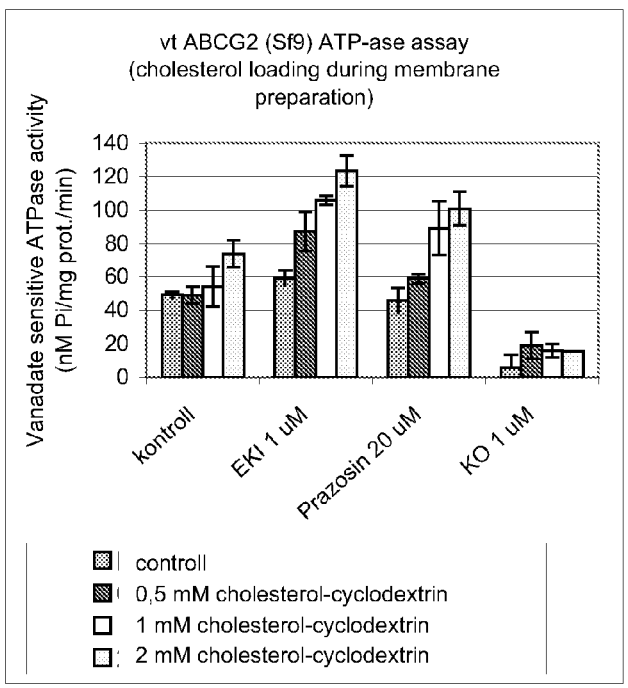
Fig. 9.b
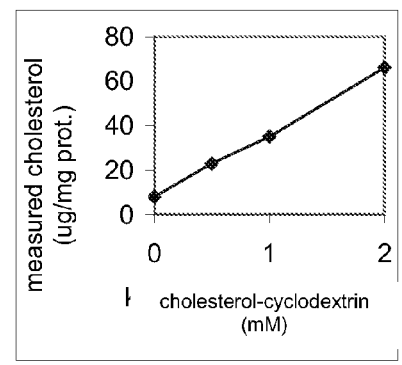

Panel II.

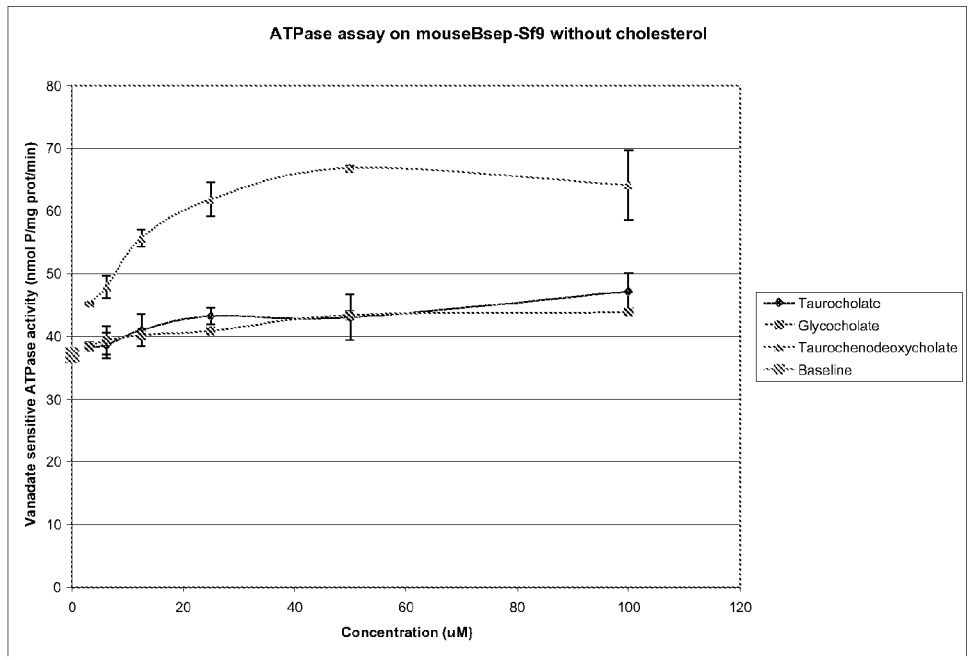
Figure 14.a
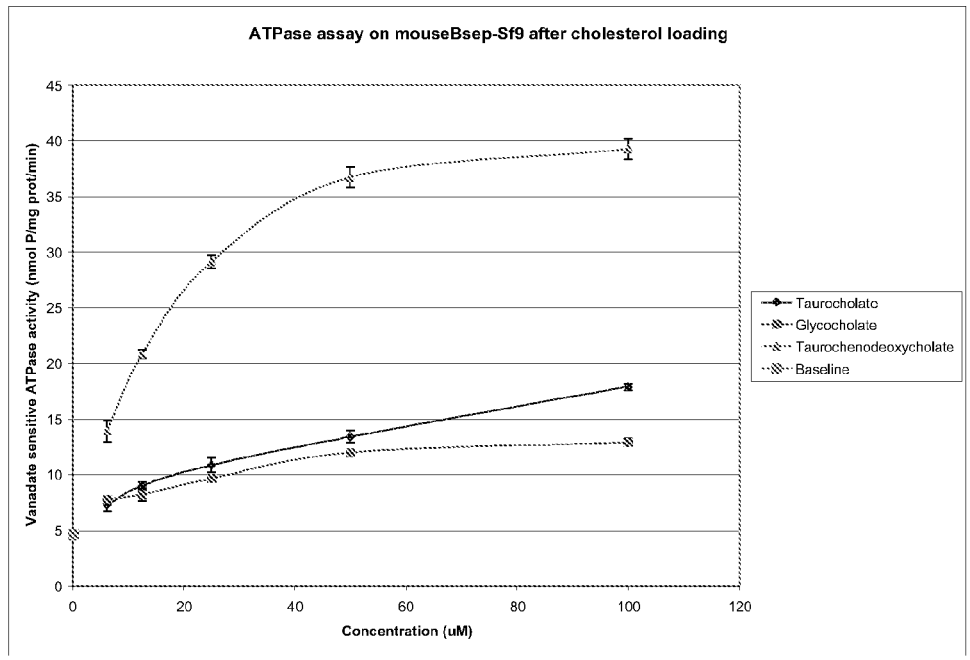
Figure 14.b

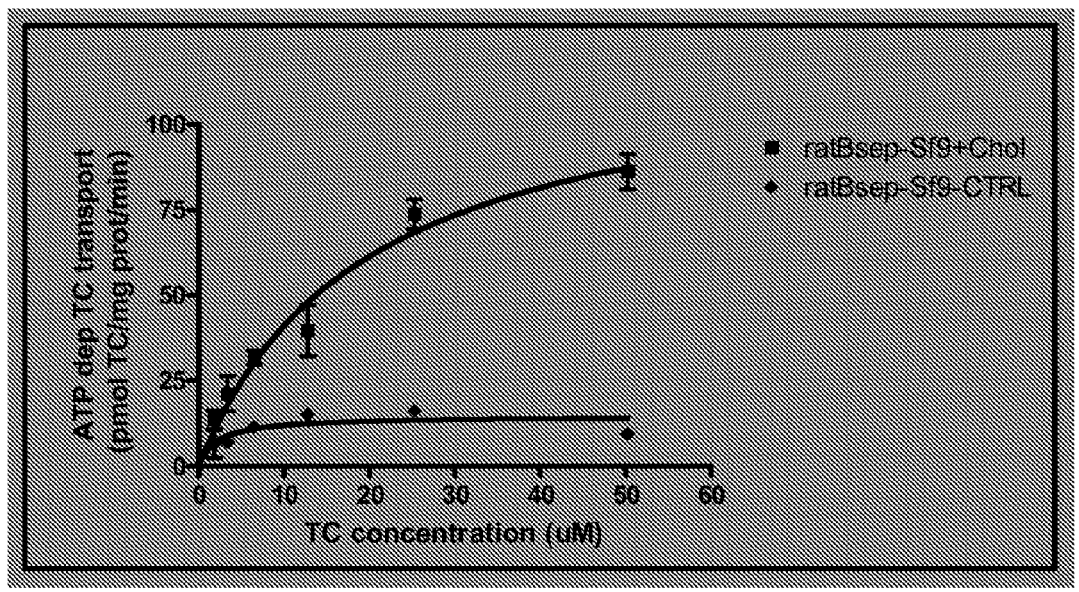
Figure.15.a
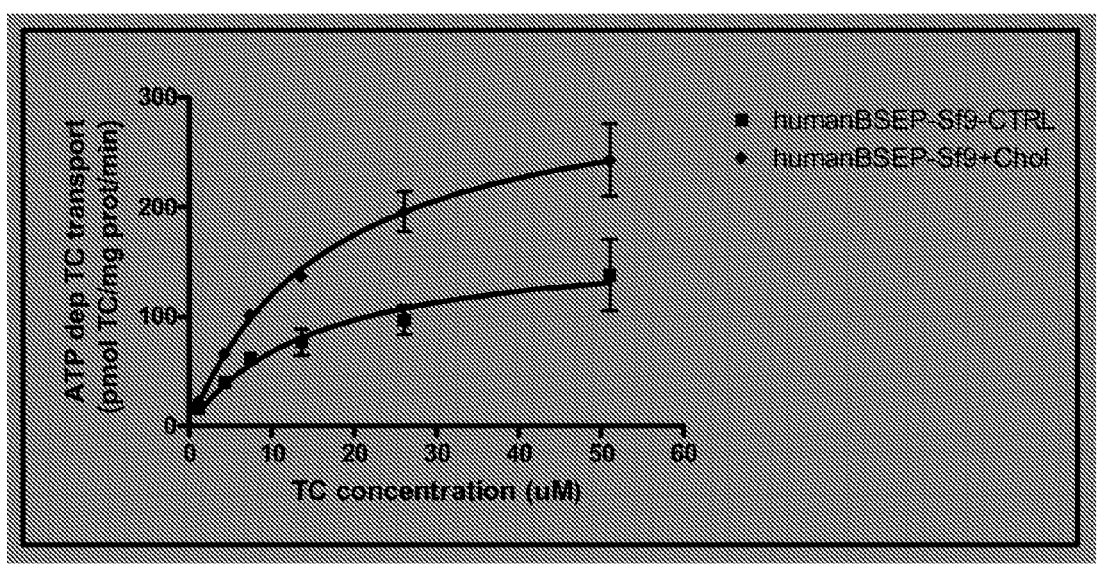
Figure 15.b

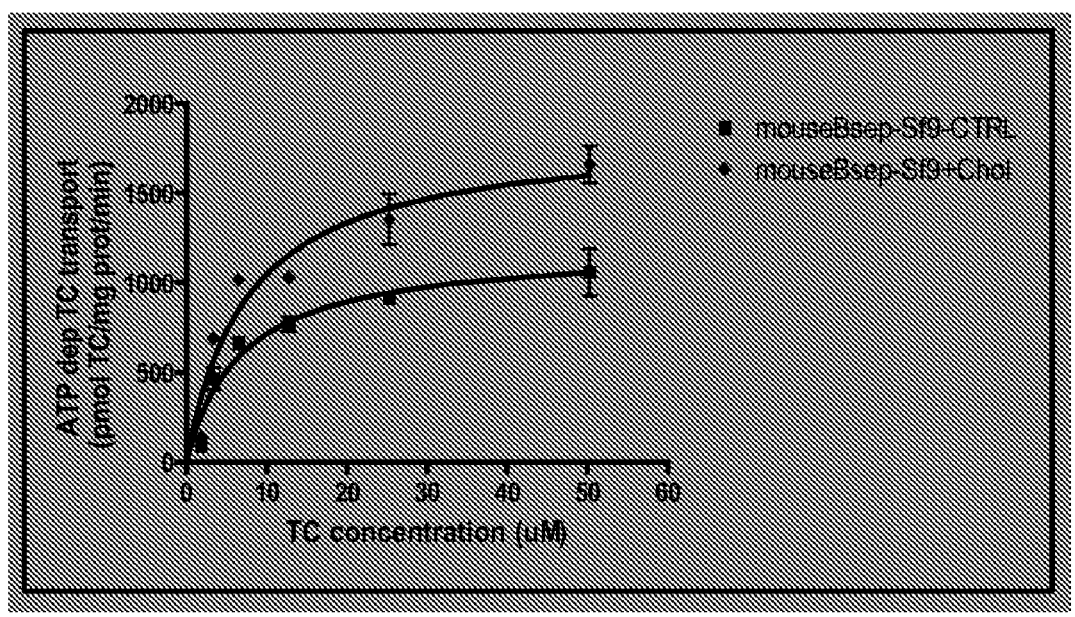
Figure 15/c

CHOLESTEROL LOADED INSECT CELL MEMBRANES AS TEST PROTEINS

This is the National Stage of International Application PCT/HU2007/000041, filed May 14, 2007.

The invention provides for a novel cholesterol loaded insect cell membrane preparation having an increased cholesterol level as compared to physiological cholesterol levels of insect cell membranes or to control insect cell membrane preparations without cholesterol loading, wherein said cholesterol loaded membrane preparation comprises an ABC transporter protein having an increased substrate transport activity due to increased cholesterol level of the membrane. The invention also relates to reagent kits comprising the preparations of the invention. The invention also relates to methods for manufacturing said preparation and methods for measuring any type of activity of the ABC transporters present in the cholesterol loaded membranes, methods for studying or testing compounds and interaction of compounds and ABC transporters in this assay systems, as well as methods for increasing substrate transport activity of ABC transporters by increasing cholesterol level of membranes. The invention also provides for a test system useful for testing whether ABC transporter proteins can be activated by cholesterol in an insect cell membrane.

BACKGROUND ART

ABC Transporter Proteins

The proteins of the ATP binding cassette (ABC) transporter superfamily form the largest family of the transmembrane proteins. Most of them are transporter proteins that use the energy from ATP hydrolyses to pump substrates through intra- and extracellular membranes. The transport in most cases is unidirectional; eukaryotes usually efflux substrates from the cytoplasm to the extracellular matrix. The transporter family includes many members (currently 49 human ABC proteins are known) that were classified after phylogenetic analysis into 7 subfamilies (from ABCA-ABCG) [Dean, M, Rzetsky, A és Allikmets R., "The Human ATP-Binding Cassette (ABC) Transporter Superfamily", Genome Res. 2001 11, 1156-1166]. ABC transporters play a pivotal role in keeping the body healthy and functioning. Their deficiency or malfunction can lead to diseases, like hereditary diseases. The research focusing on their physiological role is still at a relatively early stage.

Within the ABC transporter superfamily several transporters act as a multidrug resistant transporter. Multidrug resistant transporters are transporter proteins that are able to extrude from the cell by active transport a variety of xenobiotics, including drugs. In many cases increase of their activity can lead to resistance against drug therapy. Several members of the transporter family, e.g. MDR1, MRP1 and ABCG2 (MXR/BCRP) have been demonstrated to play a role in the development of drug resistance. The transporters significantly influence the kinetics of drug absorbtion even without any overexpression or activity amplification. As several drugs are substrates of a multidrug transporter, during drug development it is of crucial importance to exclude from the circle of potential drug candidate molecules those ones that can be substrates of such transporters, already at an early phase (early ADME, an acronym for "Absorption, Distribution, Metabolism, Excretion").

Assays for Studying Membrane Transporters

Membrane transporters are commonly studied in cellular or membrane based assays. To membrane assays the transporters of interests are overexpressed in cellular systems and following expression of the transporters, membrane preparations are isolated from these cells. Insect cell based expression systems, like the insect-Baculovirus system, are frequently applied for protein expression. Insect cells are most frequently derived from the ovary cells of the moth, *Spodoptera frugiperda*; Sf9 cells are one example.

Thus, the methods for the investigation of the ABC transporters are particularly important; membrane assays are commonly applied for this purpose. Solvo, the applicant itself is also distributor of several membrane assays that are suitable to study interactions between transporters and candidate or lead drugs. Solvo has developed a membrane assay using membranes derived from mammalian cells expressing ABCG2 (MXR-M).

The activity of the transport is usually measured i) either by the rate of ATP consumption ii) or the transport of labeled substrates is monitored. In ATPase assays (i) the transport itself is not measured directly, but via substrate stimulation of ATPase activity, because transported substrates enhance the ATPase activity so they are also referred to as activators. Among transport assays (ii) the determination of vesicular transport is particularly important in the study of transporters. In this assay inside-out vesicles from insect cell membranes are used; and the substrate is transported into the vesicle, where it accumulates and can be detected.

It is of pivotal importance that in vitro models closely mimic the physiological phenotype.

Membranes prepared from human or other mammalian expression systems have been widely used in the field of ABC transporters. Unfortunately, these expression systems usually yield significantly lower expression levels that are insufficient to measure the ATPase activity of the transporter. Moreover, while the transporter to be assayed should be overexpressed, other transporters expressed by the mammalian host cell may contribute to the background or result in a disturbing effect, in particular if the substrate specifities of the transporter proteins overlap.

More robust insect cell expression systems provide usually higher expression rates, and have the clear advantage of being free of other transporters, thus one and only one type of transporter protein can be studied. Assays based on insect cell membrane preparations are particularly preferred as being stable, reliable, easy to handle and quite often several assay formats (substrates stimulated ATPase, vesicular transport and/or nucleotide occlusion) are offered.

Otherwise effective and convenient insect cell and insect cell membrane preparation based assays, however, show certain disturbing differences as compared to mammalian cell based assays, which question their value as a useful and relevant assay system in drug development.

It has been reported for certain ABC transporters, e.g. in case of MDR1 (ABCB1) and ABCG2 as well, that a high basal ATPase activity renders substrate stimulated ATPase assays less sensitive. It has been suggested that the basal ATPase activity, measured in the absence of added substrates, may be due to activation by endogenous substrates, or may reflect a partially uncoupled ATPase activity of the transporter [M. M. Gottesman, T. Fojo, S. E. Bates, Multidrug resistance in cancer: role of ATP-dependent transporters, Nat Rev Cancer 2 (2002) 48-58; G. Szakacs, J. K. Paterson, J. A. Ludwig, C. Booth-Genthe, M. M. Gottesman, Targeting multidrug resistance in cancer, Nat Rev Drug Discov 5 (2006) 219-234]

A surprisingly large difference in the activity of the transporters and the sensitivity for different substrates (sulfasalazine, topotecan, prazosin, mitoxantrone and methotrexate) was observed between the assays based on mammalian or insect cell membranes. Moderated activity and decreased substrate sensitivity for activators/substrates were observed for several transporters expressed in Sf9 membranes. For certain substrates the transporter showed no activity when measured with insect cell derived vesicles.

For example, in case of the wild type ABCG2 transporter, in spite of a pronounced basal ATPase activity, the substrate drug stimulation in the Sf9 cell membranes was relatively small. In contrast, in isolated mammalian cell membranes, ABCG2-ATPase activity could be significantly stimulated by various drug substrates. It was also reported that ATPase activity of the wt ABCG2 protein could not be stimulated by prazosin, a known ABCG2 substrate, when expressed in insect cell membranes [Ishikawa, T., Kasamatsu, S., Hagiwara, Y., Mitomo, H., Kato, R. and Sumino, Y. (2003) Expression and functional characterization of human ABC transporter ABCG2 variants in insect cells. Drug Metab Pharmacokinet 18: 194-202.; Ozvegy, C., Litman, T., Szakacs, G., Nagy, Z., Bates, S., Varadi, A. and Sarkadi, B. (2001) Functional characterization of the human multidrug transporter, ABCG2, expressed in insect cells. Biochem Biophys Res Commun 285: 111-117.]

Since membrane proteins, when expressed in Sf9 cells are underglycosylated, it was speculated that the loss of glycosylation may result in these alterations of the ABCG2-ATPase activity. In respect of ABCG2 it has been demonstrated that glycosylation has no effect either on its activity, processing, or membrane localization [K. Mohrmann, M. A. van Eijndhoven, A. H. Schinkel, J. H. Schellens, Absence of N-linked glycosylation does not affect plasma membrane localization of breast cancer resistance protein (BCRP/ABCG2), Cancer Chemother Pharmacol 56 (2005) 344-350.; N. K. Diop, C. A. Hrycyna, N-Linked glycosylation of the human ABC transporter ABCG2 on asparagine 596 is not essential for expression, transport activity, or trafficking to the plasma membrane, Biochemistry 44 (2005) 5420-5429.]

So far no direct studies have been conducted to compare the biochemical characteristics of transporters expressed in Sf9 and human systems.

Thus, there is a permanent need in the art for insect cell based and in particular insect cell membrane preparation based ABC transporter assays which have improved physiological relevance and/or improved efficiency.

The present inventors applied a new approach when tried to upload insect cell membranes with cholesterol.

Interaction of Cholesterol with ABC Transporters

As to the interaction of cholesterol with specific ABC transporters, previously it has been suggested that MDR1 (ABCB1, P-glycoprotein or P-gp) is located in the raft/calveola domain and its activity under certain conditions is cholesterol dependent [Troost J, Lindenmaier H, Haefeli W E, Weiss J. "Modulation of cellular cholesterol alters P-glycoprotein activity in multidrug-resistant cells" Mol Pharmacol. November 2004; 66(5):1332-9.].

Related to this phenomenon, Kamau S W and coworkers (In Vitro Cell Dev Biol Anim, 2005 41(7) 207-16) have found that cholesterol depletion influences the composition of the membrane lipid, modulates the localization of P-gp and causes its loss of function. The amount of P-gp in the membrane decreased as a result of cholesterol depletion and moved from the "raft" fraction into the fraction that has higher density.

In the U.S. Pat. No. 6,855,812 patent application Hanscom and coworkers describe procedures based on P-glycoprotein. Though they were aware of cholesterol influencing the expression of specific ABC transporters, nonetheless they did not suggest any difference in activities thereof and they were silent about the application of cholesterol to increase activity of ABC transporters or efficiency of the membrane assays.

In fact, MDR1 is the only ABC transporter where the effect of cholesterol on transporter activity has been investigated in detail [Garrigues, A., Escargueil, A. E. and Orlowski, S. (2002) The multidrug transporter, P-glycoprotein, actively mediates cholesterol redistribution in the cell membrane. Proc Natl Acad Sci USA. 99: 10347-10352.] It has been suggested that cholesterol is an ABCB1 substrate, a conclusion challenged lately [Le Goff, W., Settle, M., Greene, D. J., Morton, R. E. and Smith, J. D. (2006) Reevaluation of the role of the multidrug-resistant P-glycoprotein in cellular cholesterol homeostasis. J Lipid Res 47: 51-58.]

It has been proposed for other transporters too, that at least partially they are localized in raft/caveolar systems. Yunomae and coworkers suggested that the inhibitory effect of dimethyl-beta-cyclodextrin on P-gp and MRP2 function could be attributed to the release of these transporters from the apical membranes into the medium as secondary effects through cholesterol-depletion in caveolae while had no effect on the mRNA levels. Thus, no direct effect of cholesterol to activity was observed [Yunomae K, Arima H, Hirayama F, Uekama K. Involvement of cholesterol in the inhibitory effect of dimethyl-beta-cyclodextrin on P-glycoprotein glycoprotein and MRP2 function in Caco-2 cells. FEBS Lett. Feb. 11, 2003; 536(1-3):225-31.].

Among the other membrane transporters primarily the known cholesterol transporter ABCA1 (ABC1) was investigated. Feng, Bo and Tabas, Ira (J. Biol. Chem. 2002 277(48) 43271-43280) have described that the ABCA1 mediated cholesterol and phospholipids efflux was initially induced in cholesterol loaded macrophages, however, later with the accumulation of free (not esterified) cholesterol (which process parallels with the progression of atherosclerotic lesions) it is inhibited and the level of ABCA1 protein also decreases.

Several patent applications [e.g. WO 00/18912 (Schmitz G and Klucken J.), U.S. Pat. No. US 2004/0096851 (Wang N. et al.), U.S. Pat. No. 6,617,122 (Hayden M. R. et al.)] describe the effect of cholesterol on the expression of different ABC transporters. According to our knowledge none of these, however, describe or even mention that cholesterol itself would enhance transport activity.

In US 2004/0185456 the authors (Denefle P. and co.) in example 17 of the description assays are described for the identification of ABC1 protein agonists and antagonists. Vesicles containing the substrates of the protein (e.g. cholesterol and phospoholipid) are applied. No indication has been made however, on the effect of the above mentioned substrates on the activity of ABC1.

Thus, the only observation in the art regarding the effect of cholesterol on the activity of an ABC transporter protein, even if results are somewhat contradictory, concerns MDR1. Nevertheless, in all of these experiments it seems that the authors used mammalian cells or membranes prepared from them. As mentioned earlier, none of the authors refer to the potential application of cholesterol to enhance the activity of ABC transporters, moreover, they do not even suggest the need for such procedure.

In an effort to improve performance of insect cell membrane the present inventors decided to start with the only ABC transporter reported in the art to possibly have a cholesterol sensitive transport capability, i.e. MDR1. They found that membrane cholesterol modulation had only a negligible effect on the activity of the MDR1 multidrug transporter. The conclusion that no improvement of insect cell or insect cell membrane preparation based assays on ABC transporters is possible by cholesterol upload of insect cell membranes was necessarily drawn.

Despite discouraging results the present inventors were unexpectedly able to prepare insect cell membrane preparations and insect cells loaded with cholesterol comprising ABC transporters having increased transport activity in such cholesterol loaded membranes as compared to insect cell membranes comprising the normal level of cholesterol.

In particular, the present inventors unexpectedly found that insect cells or the membrane preparations derived from them, constructed by insect expression systems expressing ABC transporters, like wild type ABCG2 or BSEP (ABCB11), that the activity of the transporter and/or its ligand sensitivity can be increased by increasing the cholesterol content of the membrane. The inventors found that typically cholesterol loading induced activation of the assay systems based on Sf9 cell membranes in both substrate stimulated ATPase and vesicular transport assays.

BRIEF DESCRIPTION OF THE INVENTION

The invention relates to a cholesterol loaded insect cell membrane preparation comprising an increased cholesterol level as compared to the physiological cholesterol level of the same type of insect cell membrane, said insect cell membrane preparation comprising an active membrane transporter protein, preferably an ABC transporter protein. Said transporter protein preferably has an increased substrate transport activity or substrate sensitivity as compared to the substrate transport activity or substrate sensitivity of said transporter protein if present in the same type of insect cell membrane having a physiological cholesterol level. Alternatively, the invention relates to a cholesterol loaded insect cell membrane preparation having an increased cholesterol level as compared to a control insect cell membrane preparation without cholesterol loading, wherein said cholesterol loaded membrane preparation comprises a membrane transporter, preferably an ABC transporter protein having an increased substrate transport activity or substrate sensitivity as compared to the substrate transport activity or substrate sensitivity of the same ABC transporter protein if present in the control insect cell membrane preparation.

The term cholesterol involves herein any cholesterol analogue or cholesterol derivative.

The invention further relates to a cholesterol loaded insect cell preparation comprising an increased cholesterol level as compared to the physiological cholesterol level of the membrane of the same type of insect cell, said insect cell preparation comprising a membrane transporter, preferably an ABC transporter protein. Said transporter preferably has an increased substrate transport activity or substrate sensitivity as compared to the substrate transport activity or substrate sensitivity of said ABC transporter protein if present in the membrane of the same type of insect cell having a physiological cholesterol level.

Preferably, in the preparations of the invention the cholesterol level is
- at least 50%, preferably at least 60%, more preferably at least 80% of the corresponding cholesterol level of a mammalian cell membrane,
- at least 2 times, preferably at least 3 times, more preferably at least 4 times, highly preferably at least 6 times of that of the physiological cholesterol level of an insect cell membrane,
- calculated as the cholesterol content relative to the total protein content and is at least 25 µg/mg total protein, preferably at least 50 µg/mg total protein.

Preferably, the substrate transport activity or substrate sensitivity of the membrane transporter, preferably ABC transporter protein is tested by a) a vesicular transport assay and/or b) a substrate stimulated ATPase assay. Preferably, the substrate transport activity or substrate sensitivity of the ABC transporter protein is significantly, preferably at least 1.5 times, preferably at least 2 times, more preferably at least 3 times, highly preferably at least 5 times or even 10 times higher than the substrate transport activity or substrate sensitivity of said ABC transporter protein if present in a control insect cell membrane preparation of the same type having a physiological cholesterol level.

In a highly preferred embodiment the ABC transporter protein is ABCG2. In a still further highly preferred embodiment the ABC transporter protein is BSEP.

According to a further embodiment the invention relates to a reagent kit for assessing activity of an ABC transporter protein, said kit comprising
- the preparation according to the invention, and/or
- means for expressing said ABC transporter in insect cells and means for loading the insect cells with cholesterol and/or a cholesterol analogue, and optionally means for preparing a membrane preparation from the insect cells, and
- if desired, any of the following: substrates of the ABC transporter protein, ATP, cholesterol or cholesterol analogues, buffers, reagents, controls, inhibitors or activators of the ABC transporter protein.

The invention further relates to a method for manufacturing an insect cell preparation or an insect cell membrane preparation comprising an ABC transporter protein having increased substrate transport activity or substrate sensitivity, for use in an ABC transporter protein assay, wherein said method comprises
- providing an ABC transporter protein having substrate transport activity or substrate sensitivity in an insect cell preparation or an insect cell membrane preparation,
- loading the insect cell preparation or the insect cell membrane preparation with cholesterol thereby increasing cholesterol level of the insect cell preparation or the insect cell membrane preparation,
- testing the obtained cholesterol loaded insect cell preparation or insect cell membrane preparation for increased substrate transport activity or substrate sensitivity of the ABC transporter protein as compared to the same activity in cholesterol unloaded insect cell preparation or insect cell membrane preparation of the same type.

In a preferred variant of the method of the invention
- the cell membrane preparation is prepared from insect cells comprising the ABC transporter protein and
- the cell membrane preparation is incubated with a complex of cyclodextrin and the cholesterol or cholesterol analogue, and
- unbound complex is removed.

In a further variant of the method
- the ABC transporter protein is expressed in insect cells,
- the insect cells either before or during expression of the ABC transporter protein are incubated with a complex of cyclodextrin and the cholesterol or cholesterol analogue,
- unbound complex is removed, and
- a cell membrane preparation is prepared from the insect cells.

In a highly preferred variant of the method
the ABC transporter protein is expressed in insect cells,
the cell membrane preparation is prepared from the insect cells, comprising at least the following steps
   i) membrane isolation,
   ii) homogenization,
   iii) incubation of the homogenized preparation with a complex of cyclodextrin and the cholesterol or cholesterol analogue, and
   iv) ultracentrifugation.

Highly preferably, the increased substrate transport activity of the ABC transporter protein is tested by
   a) a vesicular transport assay and/or
   b) a substrate stimulated ATPase assay.

Highly preferably, the ABC transporter protein is ABCG2 or BSEP.

The invention also relates to an insect cell preparation or an insect cell membrane preparation comprising an increased cholesterol level as compared to the physiological cholesterol level of insect cell membranes and an ABC transporter protein of increased substrate transport activity or substrate sensitivity as compared the substrate transport activity or substrate sensitivity of said ABC transporter protein in an insect cell membrane having physiological cholesterol content, wherein said insect cell preparation or said insect cell membrane preparation is obtainable by the method of the invention.

The invention also relates to a method for increasing ABC transporter activity by increasing cholesterol content or level of a membrane comprising the ABC transporter protein. In this method any methods described herein can be applied.

The invention also relates to an assay method for studying interaction of a compound and an ABC transporter protein by assessing activity of said ABC transporter protein, wherein said assay method comprises the steps of
   providing an active ABC transporter protein in an insect cell or in an insect cell membrane preparation,
   contacting a compound with the ABC transporter protein,
   measuring any activity of the ABC transporter protein in the presence and in the absence of said compound,
   comparing the activity values obtained in the presence and in the absence of the compound,
   wherein
   the insect cell preparation or the insect cell membrane preparation has an increased cholesterol level as compared to the physiological cholesterol level of insect cell membranes.

The invention also relates to an assay method for testing simultaneous interaction of at least two compounds and an ABC transporter protein by assessing activity of the transporter protein, said method comprising at least the steps of
   providing an active ABC transporter protein in an insect cell or in an insect cell membrane preparation,
   contacting a first compound with the ABC transporter protein,
   measuring an activity of the ABC transporter protein in the presence and in the absence of said first compound,
   comparing the activity values obtained in the presence and in the absence of said first compound,
   contacting a second compound with the ABC transporter protein in the presence of the first compound,
   measuring the activity of the ABC transporter protein in the presence of the first and second compound simultaneously,
   comparing the activity values obtained in the presence and in the absence of the second compound,
   evaluating the effect of the second compound to the activity in the presence of the first compound,
   wherein
   the insect cell preparation or the insect cell membrane preparation has an increased cholesterol level as compared to the physiological cholesterol level of an insect cell membrane.

In a preferred assay method of the invention at least one of the following is determined
   substrate transport activity of the ABC transporter protein, preferably substrate stimulated ATPase activity of the ABC transporter, and/or vesicular transport of a substrate by the ABC transporter,
   nucleotide occlusion/trapping by the ABC transporter,
   basal ATPase activity of the ABC transporter.

In a further preferred assay method of the invention an insect cell preparation or an insect cell membrane preparation according to the invention is used, and/or the insect cell preparation or an insect cell membrane preparation is prepared according to any of the preparation methods of the invention.

In the assay methods of the invention the ABC transporter protein is ABCG2 and/or BSEP.

The invention also relates to a use of cholesterol or a cholesterol analogue for increasing activity of an ABC transporter protein embedded in an insect cell membrane in an insect cell preparation or in an insect cell membrane preparation. Preferably, the ABC transporter protein is tested by a) a vesicular transport assay and/or b) a substrate stimulated ATPase assay. Preferably, cholesterol is used in the form of a complex of cholesterol and a cyclodextrin.

According to a preferred embodiment, the ABC transported applied in the present invention is different from MDR1 (ABCB1).

According to a preferred embodiment of the invention the transporter, preferably the ABC transporter comprises a cholesterol binding region. In a preferred embodiment The ABC transporter useful according to the invention is capable of interacting with cholesterol at their region involved in catalysis and transport. In a further preferred embodiment, cholesterol increases nucleotide occlusion in respect of the ABC transporter The invention also provides for a test system useful for testing whether ABC transporter proteins can be activated by cholesterol in an insect cell membrane. In this embodiment of the invention any assay or measurement method to detect or assess an activity of the ABC transporter said activity correlating or corresponding to substrate transport activity of the protein, is useful to decide whether addition of cholesterol has increased ABC transporter, and can be applied. Preferably, according to this assay method the ABC transporter is provided in an insect cell preparation or in an insect cell membrane preparation loaded with cholesterol and a respective control preparation unloaded with cholesterol, and activity values obtained for the cholesterol loaded preparation and for the control preparation are compared, and if the former is higher, preferably significantly higher, preferably at least 1.5 times, preferably at least 2 times, more preferably at least 3 times, highly preferably at least 5 times higher than that obtained for the control sample, the ABC transporter is useful in the present invention.

Definitions

A cholesterol analogue is a sterol derivative that has a chemical structure that comprises an essential element of the chemical structure cholesterol and which hold at least one functional features, preferably one or more of the following features of cholesterol: bind to the cholesterol binding domain of a transporter, influence the fluidity of membranes, accumulate in membrane regions with higher cholesterol contents than that in their environment (rafts or caveoli or other), substrate of transporters that transport cholesterol as substrate. Such cholesterol analogues are for example, but not exclusively steroid hormones.

A cholesterol derivative means a cholesterol analogue that has a chemical structure that can be derived from substitution or addition, and retains at least one functional characteristics of cholesterol, preferably one or more of the following characteristics: bind to the cholesterol binding domain of any transporter, influence the fluidity of membranes, accumulate in membrane regions with higher cholesterol contents than that in their environment (rafts or caveoli or other), substrate of transporters that transport cholesterol as substrate. Such cholesterol derivatives are for example, but not exclusively 2,2-hydroxi-cholesterol, 20,22-dihydroxicholesterol, 25-hidroxycholesterol, their R and S forms, keto-variants, halogen or pseudohalogen analogues and derivatives etc.

According to a preferable variant the cholesterol analogues or derivatives using a suitable detection methodology can be detected or can be quantified with cholesterol. For example, the method applied can be chromatography, where cholesterol and the cholesterol analogue is eluated partially or completely together; or a spectroscopic method where a characteristic component of the spectrum of cholesterol and the cholesterol analogue overlap.

The cholesterol content of a membrane means the overall detectable cholesterol content or the combined quantity of cholesterol and cholesterol analogues (like cholesterol derivatives) in certain cases, the cholesterol content measured by any method appropriate to detect—preferably quantitatively—cholesterol by which all cholesterol and cholesterol analogues, like cholesterol derivatives can be determined together.

Cholesterol loading means increasing the cholesterol content or cholesterol level of a membrane, including cholesterol analogue or cholesterol derivative content or level.

A cholesterol loaded membrane or cell is a membrane or cell which has undergone cholesterol loading to increase its cholesterol content.

The physiological cholesterol content or level of a cell membrane—like membrane or membrane preparations of living cells means the cholesterol content that develops in the cell membrane or in any membrane preparations derived from such cells, with no artificially induced cholesterol loading or depletion, for example during cell culture—in a medium without cholesterol or without supplementing cholesterol, including, as above, cholesterol analogues and cholesterol derivatives. This definition also includes membrane domains. For example, the physiological cholesterol content of insect membranes depending on the cell type is around one tenth compared to mammalian cell membranes.

An ABC transporter protein has "substrate transport activity" when, under appropriate conditions, it is capable of transporting a substrate of said transporter through the biological membrane in which said transporter is present. Thus, substrate transport activity is an inherent biological property of the ABC transporter protein which is independent from the fact whether it is possible to measure or detect said activity. Substrate transport activity of an ABC transporter protein typically may be detected or measured by one or more of the following assays: cellular or vesicular transport assay, wherein it is usually possible to directly show the transport of the substrate, or substrate stimulated ATPase assay which is typically, if assay conditions are appropriately set, indicative of substrate transport. Most often vanadate sensitive or inhibitor sensitive ATPase assays are used. Substrate sensitivity specifically relates to activity as measured by substrate stimulated ATPase assay.

BRIEF DESCRIPTION OF THE FIGURES

FIG. 1.A: Vanadate sensitive ATPase activity of active ABCG2 containing insect membranes [ABCG2-Sf9 (A)] in the presence of different concentrations of substrates. FIG. 1.B: Vanadate sensitive ATPase activity of active ABCG2 containing mammalian cell membranes [ABCG2-M (B)] in the presence of different concentrations of substrates. Membrane preparations containing 20 μg membrane protein was incubated at 37° C. for 40 minutes with different concentrations of test compounds, and than the vanadate sensitive ATPase activity was determined. FIG. 1.C: ABCG2-Sf9 (▲) and ABCG2-M (■) membranes were loaded with cholesterol by treatment with cholesterol@RAMEB complex. Membrane cholesterol content was determined by the cholesterol oxidase method. Concentrations on X axis represent the total cholesterol concentration in the incubation medium. FIG. 1.D: Cyclodextrin-mediated cholesterol depletion of ABCG2-Sf9 (▲) and ABCG2-M (■) membranes was carried out by incubating the membranes for 30 min at 37° C. in the presence of RAMEB at concentrations indicated in the figure. FIG. 1.E and FIG. 1.F: optimization of cholesterol loading. Basal (●) and sulfasalazine stimulated (▲) activities were monitored after completing the loading procedure. For optimizing the incubation time (E) ABCG2-Sf9 membranes were incubated in the presence of cholesterol@RAMEB (2 mM total cholesterol in the incubation medium) for times indicated in the figure. For optimization of cholesterol loading (F) ABCG2-Sf9 membranes were incubated in presence of various cholesterol concentrations for 1 hour. ABCG2-ATPase activity data represent mean±S.D. of duplicate measurements.

—FIG. 2.A: Sf9 membrane vesicles activated by sulfasalazine. Upper curve cholesterol loaded vesicles; lower curve untreated control. FIG. 2.B: Activation of vesicles originating from mammalian membranes by sulfasalazine. The lower curve shows the residual activity of mammalian cells following depletion of cholesterol by cyclodextrin. Upper curve shows the untreated control cells.

FIG. 2.C, D, E, F: To test substrate stimulation by topotecan and prazosin, the ABCG2-ATPase activation of cholesterol loaded (▲) and control (●) ABCG2-Sf9 membranes (C and E) as well as cholesterol depleted (▲) and control (●) ABCG2-M membranes (D and F) upon topotecan (C and D) and prazosin (E and F) treatment (40 min, 37° C.) was determined. Data represent mean±S.D. of triplicates.

FIG. 3.B: Increase of methotrexate uptake in cholesterol treated vesicles (experimental design: 100 µM methotrexate; 50 µg/well protein content; 12 minutes incubation time).

In FIG. 3.C the cholesterol content of vesicles used in the experiments is shown.

FIG. 4: Effect of cholesterol loading on vesicular transport activity of ABCG2 containing ABCG2-Sf9 membranes. The amount of radiolabeled compounds retained by the inside-out vesicles was measured at various drug concentrations as indicated in the figure.

FIG. 4.A: The vesicular transport activity (methotrexate uptake) as a function of methotrexate concentration (methotrexate concentration curve, 50 µg/well protein content, 12 minutes incubation time).

FIG. 4.B: Prazosin uptake of cholesterol loaded (▲) and control (●) inside-out membrane vesicles was carried out at 37° C. for 20 min. The data were calculated as a difference of measured vesicular uptake in presence and absence of ATP. Data represent mean±S.D. of duplicates.

FIG. 8: Vanadate sensitive ATPase activity of wt ABCG2 containing Sf9 membrane preparation when cholesterol loading is carried out during the baculovirus infection step. The given quantity of cholesterol@RAMEB complex was added to the medium 24 h after the infection and was than incubated for an additional 48 hours more. The figure represents data of membranes preparations that were either untreated or were incubated with cholesterol-cyclodextrin at 3 different concentrations. 1 mM cholesterol-cyclodextrin triggered decreased transporter expression. The highest cholesterol content of the membrane preparation did not exceed 16 ug/mg protein. The effect of two substrates (EKI, Prazosin) and one specific inhibitor (Ko143) was tested at the given concentrations.

FIG. 9: FIG. 9.A shows vanadate sensitive ATPase activity of wt ABCG2 containing Sf9 membrane preparation when cholesterol loading is carried out during the membrane preparation process, following homogenization. FIG. 9.B shows the increase of cholesterol content of the membranes as a function of cholesterol-cyclodextrin concentration. The effect of two substrates (EKI, Prazosin) and one specific inhibitor (Ko143) was tested at the given concentrations.

Dark columns: vesicular MTX transport without inhibitor, striped columns: MTX transport in the presence of the specific ABCG2 inhibitor, Ko143 (1 µM).

Part 1 demonstrates MTX uptake in the unloaded, control vesicles (containing 8 µg cholesterol/mg membrane protein), Part 2 shows MTX uptake in cholesterol-cyclodextrin (C-CD) pre-treated vesicles (containing 56 µg cholesterol/mg membrane protein), and Part 3 shows MTX uptake in empty cyclodextrin (CD) pre-treated vesicles (containing 5 µg cholesterol/mg membrane protein). Part 4 shows the effect of sitosterol loading on ATP-dependent MTX uptake in Sf9 membrane vesicles, when the vesicles were pre-treated with sitosterol-beta-cyclodextrin (S-CD), similarly to the CD or C-CD pre-treatments.

The mean values±SD are presented. Significant differences are indicated by stars.

Figure 11A:
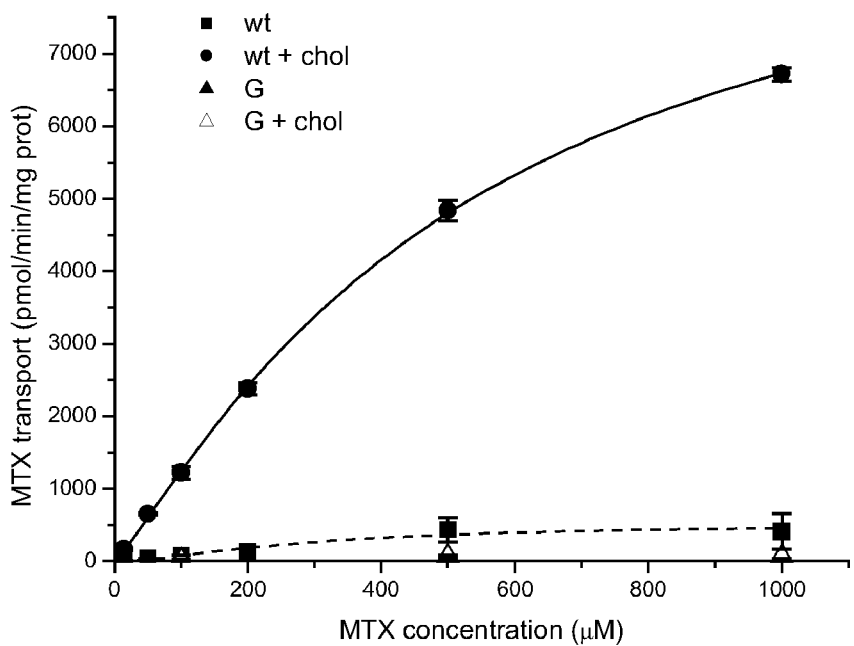
Figure 11B:
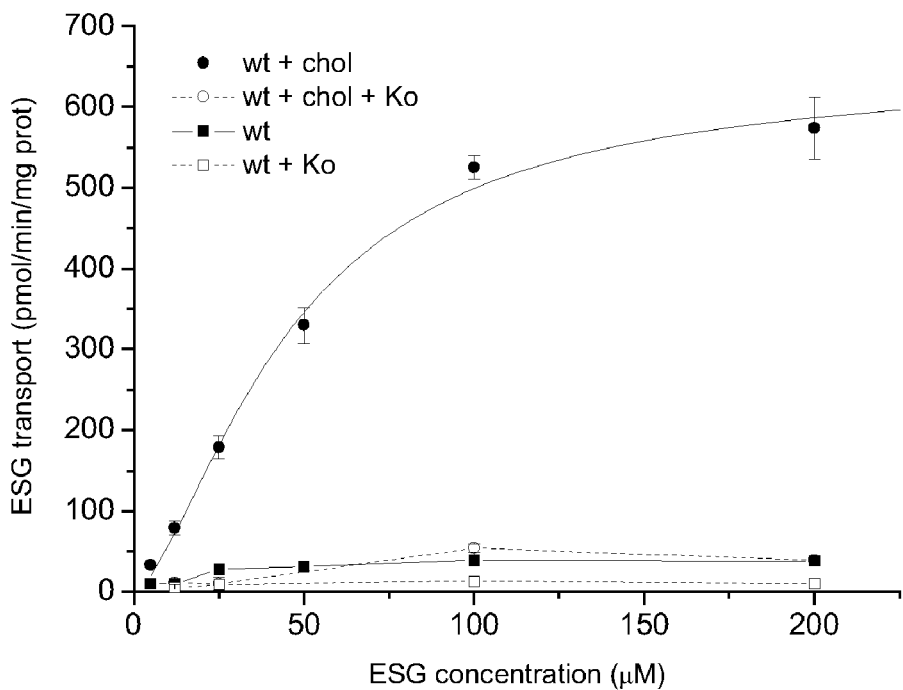
Figure 11C:
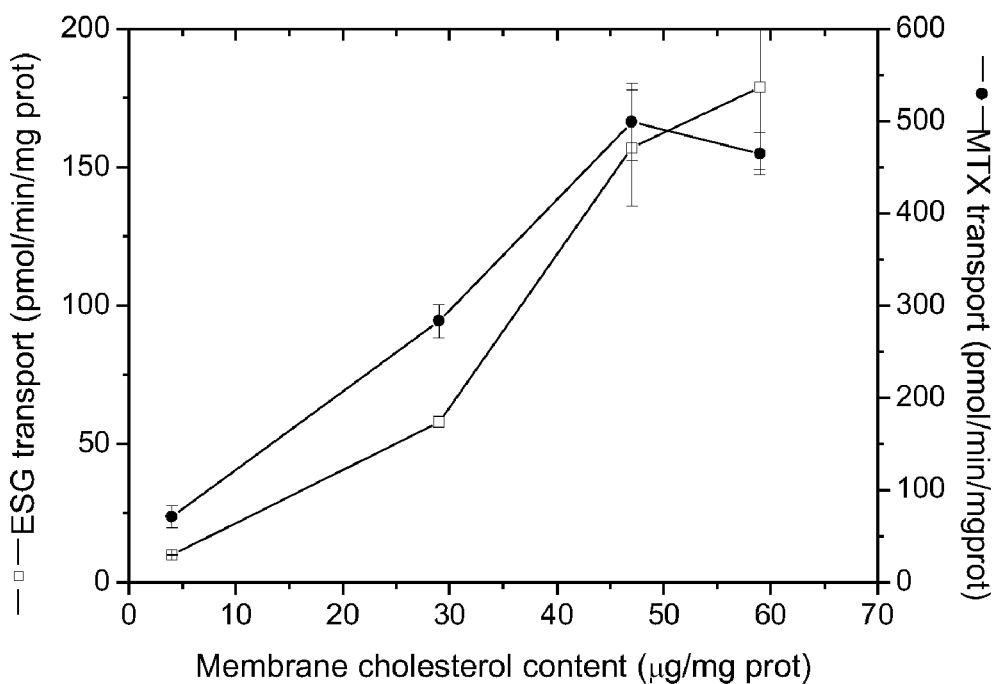

FIGS. 11A, 11B and 11C: Effect of cholesterol loading on ATP-dependent MTX and ESG uptake in Sf9 membrane vesicles.

MTX and ESG uptake was measured for 5 min at 37° C. at 5 mM ATP in membrane vesicles containing the human wild-type ABCG2 (WT), or R482G-ABCG2 (G) transporter. During this time period drug uptake was linear. The mean values±SD are presented.

FIG. 11A: MTX concentration dependence of MTX uptake. ABCG2-specific uptake at each substrate concentration was calculated by subtracting the rate obtained in the presence of 1 µM Ko143 ABCG2 inhibitor.

■—MTX uptake in the control vesicles (8 µg cholesterol/mg membrane protein), containing the human wild-type ABCG2 (WT) transporter, ●—MTX uptake in cholesterol-loaded vesicles (56 µg cholesterol/mg membrane protein), containing the human wild-type ABCG2 (WT) transporter, ▲—MTX uptake in the control vesicles (8 µg cholesterol/mg membrane protein), containing the human R482G ABCG2 (G) transporter, Δ—MTX uptake in cholesterol-loaded vesicles (62 µg cholesterol/mg membrane protein), containing the human R482G ABCG2 (G) transporter.

FIG. 11B: ESG concentration dependence of ESG uptake

■—ESG uptake in the control vesicles (8 µg cholesterol/mg membrane protein), containing the human wild-type ABCG2 (WT) transporter, □—ESG uptake in the control vesicles (8 µg cholesterol/mg membrane protein), containing the human wild-type ABCG2 (WT) transporter, in the presence of 1 µM Ko143, ●—ESG uptake in cholesterol-loaded vesicles (56 µg cholesterol/mg membrane protein), containing the human wild-type ABCG2 (WT) transporter, ○—ESG uptake in cholesterol-loaded vesicles (56 µg cholesterol/mg membrane protein), containing the human wild-type ABCG2 (WT) transporter, in the presence of 1 µM Ko143.

FIG. 11C: Relative stimulation of MTX and ESG transport by cholesterol loading in Sf9 membrane vesicles.

MTX uptake (●) was measured at 50 µM MTX concentration, while ESG transport (□) was measured at 25 µM ESG, for 5 min at 37° C., in Sf9 membrane vesicles containing the human wild-type ABCG2. Membranes from the same cell preparation, containing identical amount of ABCG2, were pre-loaded by variable C-CD concentrations to contain different levels of cholesterol. On the Figure for each data point the mean values±SD are presented.

Figure 12A:
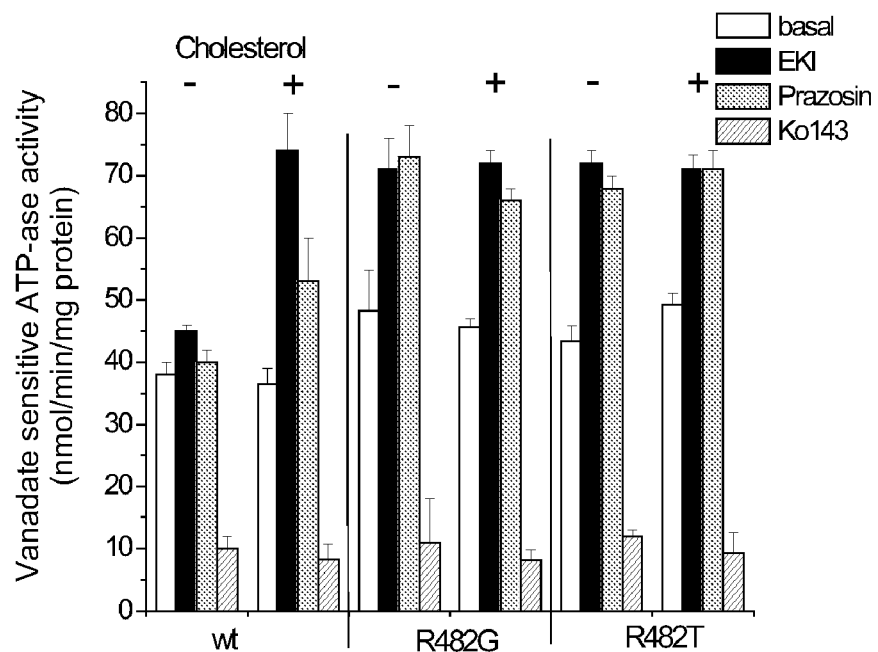
Figure 12B:
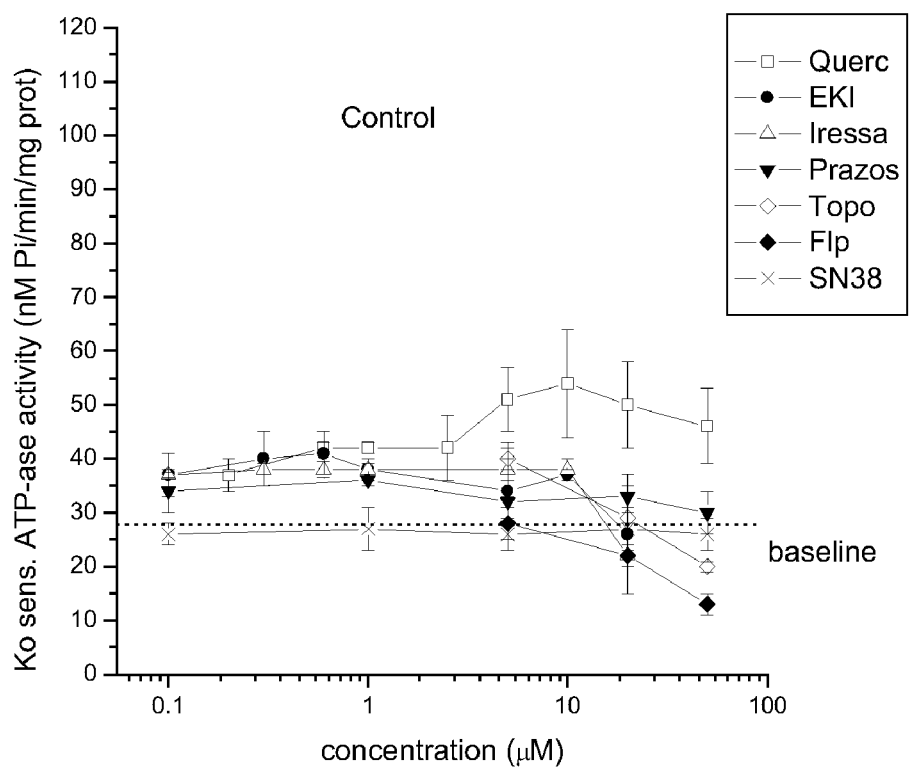
Figure 12C:
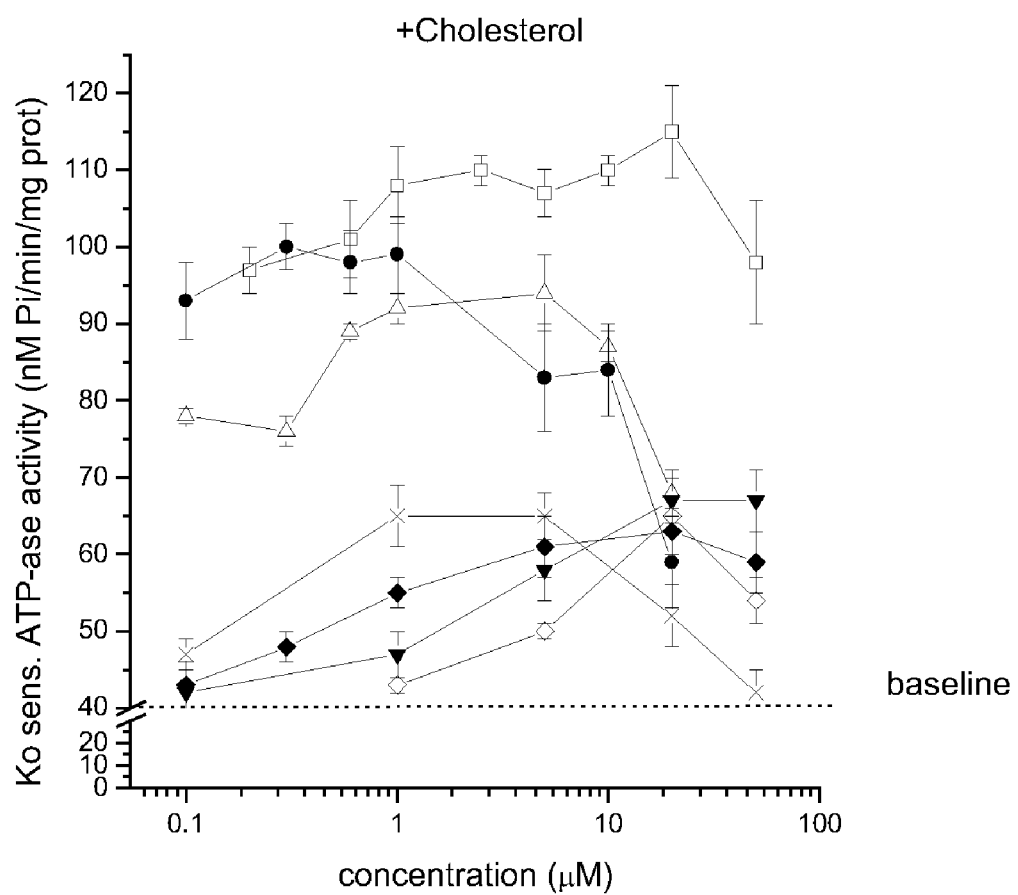

FIGS. 12A, 12B and 12C: Effect of cholesterol loading on the ATPase activity of ABCG2 in isolated Sf9 membrane preparations.

FIG. 12A: Effect of cholesterol loading on the vanadate-sensitive ATPase activity in isolated Sf9 membrane preparations. ATPase activity in the vesicles was measured for 20 min at 37° C. in membranes containing the human wild-type ABCG2 (WT), the R482G-ABCG2 (R482G), or the R482T-ABCG2 (R482T) transporter.

The basal ATPase activity and the effects of two potential substrates of the ABCG2 transporter were examined. Prazosin was applied in 20 μM concentration, EKI was used in 1 μM concentration. The effect of Ko143, a specific ABCG2 inhibitor was measured at 1 μM concentration. The mean values±SD are presented. Control membranes contained 8 μg cholesterol/mg membrane protein, while cholesterol-loaded membranes contained 56 μg cholesterol/mg membrane protein in the case of the wt ABCG2, 62 μg cholesterol/mg membrane protein in the case of the ABCG2-R48G, and 65 μg cholesterol/mg membrane protein in the case of the ABCG2-R482 T variant.

Empty columns: basal ATPase activity, black columns: 1 μM EKI, light gray columns: 20 μM prazosin, striped columns: 1 μM Ko143.

FIGS. 12B and 12C: Concentration dependence of the stimulatory effect of different drugs on the ABCG2 ATPase activity in control (B) and in cholesterol loaded (C) Sf9 cell membrane preparations. ATPase activity was measured for 20 min at 37° C. in membranes containing the human wild-type ABCG2, either without cholesterol-loading (left panel) or loaded with cholesterol (right panel). The ABCG2-specific ATPase activity was determined as the Ko143-sensitive fraction of the activity. Cholesterol loading by C-CD was achieved as described in the Methods. Each drug was tested in at least two independent membrane preparations, the mean±SD values are presented in a representative experiment with triplicate measurements. The control membranes contained 8 μg cholesterol/mg membrane protein, while cholesterol-loaded membrane vesicles contained 42 μg cholesterol/mg membrane protein.

□-Quercetin, ●-EKI-785, ∆-Iressa, ▼-Prazosin, ◇-Topotecan, ◆ Flavopiridol, X-SN-38

Figure 13:
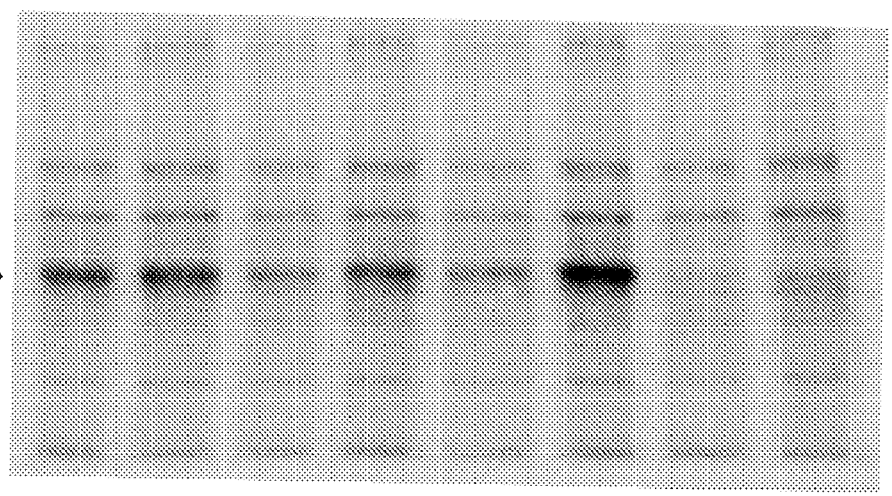

FIG. 13: Effect of cholesterol loading on the formation of the catalytic intermediate (nucleotide trapping) of human ABCG2 in isolated Sf9 membrane preparations.

8-azido-nucleotide trapping by the human, wild-type ABCG2 protein, expressed in Sf9 cell membranes, was measured as described in the Methods section, in the presence of 2.5 μM Co-8-azido-ATP (containing alpha-$^{32}$P-8-azido-ATP) at 37° C. for 2 min. Following UV-irradiation, gel-electrophoresis and electroblotting, the labeled bands were visualized by Phospho-Imager. The arrow indicates the position of the ABCG2 protein identified by immunoblotting.

Isolated Sf9 cell membranes, containing the same amount of wild-type ABCG2 protein were loaded with cholesterol by preincubation with 4 mM C-CD, as described in the Methods. Cholesterol-loaded membrane vesicles contained 50 μg cholesterol/mg membrane protein, while the control membranes contained 8 μg cholesterol/mg membrane protein. The concentration of EKI or Ko143 was 1 μM, the concentration of prazosin was 20 μM in the assay. The figure shows a representative experiment.

FIGS. 14.a and 14.b: Vanadate sensitive basal ATPase activity of untreated and cholesterol treated mouseBsep insect membrane vesicles (Sf9)

FIG. 14.a: Effect of the taurocholate (◆), glycocholate (■) and taurochenodeoxycholate (▲) on untreated mouseBsep membrane in vanadate sensitive ATPase assay in cholesterol loaded membrane vesicles. Baseline is also indicated (■).

FIG. 14.b: Effect of the taurocholate (◆), glycocholate (■) and taurochenodeoxycholate (▲) on treated mouseBsep membrane in vanadate sensitive ATPase assay. Baseline is also indicated (■).

FIGS. 15.a, 15.b and 15/c: Effect of cholesterol loading of inside-out membrane vesicles on the vesicular taurocholate (TC) transport activity of human/mouse/rat Bsep transporters; cholesterol loaded (■), control (◆), FIG. 15.a: Effect of cholesterol on ratBsep transporter's activity; cholesterol loaded (■), control (◆)

FIG. 15.b: Effect of cholesterol on humanBsep transporter's activity; cholesterol loaded (■), control (◆)

FIG. 15/c: Effect of cholesterol on mouseBsep transporter's activity; control (■), cholesterol loaded (◆)

DETAILED DESCRIPTION OF THE INVENTION

Many assays used to study the effects of drug transporters are based on membranes purified from insect cells or sometimes insect cells themselves. Viral systems useful for infect insect cells are well known in the art. Any heterologous expression systems should be used, however, with a cautious attitude as an environment different from the natural environment of the heterologous protein and correlation and validation studies are justified. However, few studies address directly this problem.

When trying to approach insect cell based assays of ABC transporter proteins to mammalian cell based ones and possibly reduce differences reported in the art, the present inventors hypothesized, that the altered glycosylation of insect and of human plasma membrane vesicles could be responsible for the differences observed in the activation profile of said transporters, such as lack of transport of substrates or increased basal ATPase activity. Deglycosylation of human wt ABCG2 expressed in human ABCG2-M membranes did not affect, however, the ATPase activity.

A further difference may reside in different membrane composition. For example, the cholesterol content of the membranes derived from Sf9 cells is low, as described earlier in the literature [Gimpl. G et al., Biochemistry 34(42), 13794-801 (1995); Kopanchuk S es Ringen A, Proc Estonian Acad Sci Chem, 50(4), 229-240] and the present inventors found that they contain 20% of that measured in mammalian membranes.

Cholesterol modulation of MDR1 (ABCB1) has been reported in the literature. However, it appears that the present inventors were the first to suggest that in such insect cell based assay systems (including membrane vesicles) increasing cholesterol content of insect cell membrane may allow to obtain transporter activities more similar to those obtained in mammalian cells.

Therefore, the present inventors have examined the effects of membrane cholesterol on the human MDR1 protein expressed in intact cells or in Sf9 cell membrane preparations in several experimental settings and found that under conditions used also in the present study, the effect of membrane cholesterol level on these transporters was negligible. More closely, it was found that the basal activity of the MDR1-ATPase was slightly increased, while the verapamil-stimulated maximum ATPase activity, measured at 50 μM verapamil, was practically unchanged in cholesterol-loaded Sf9 membranes.

Thereby, nevertheless, the present inventors created a reliable test system in which actually any ABC transporter protein which can be expressed in insect cells in active form can be tested as to whether its activity can be increased upon cholesterol (or cholesterol analogue) loading of the insect cells or insect cell membrane vesicles, depending on the assay format. Active form is understood herein preferably as being capable of transporting at least one substrate of said ABC transporter, even if this transport is undetectable in traditional insect cell or insect cell membrane assay systems or formats.

Therefore, despite negative result with the only transporter known to be cholesterol sensitive so far, the present inventors continued experimentation and found that insect cell membranes of increased cholesterol level provide an improved environment for other ABC transporters, such as ABCG2 and BSEP.

ABCG2 protein is one of the most important multidrug transporters involved in drug ADME.

Direct vesicular transport studies performed in insect cell preparations indicated that the maximum transport rate of ABCG2 can be increased even up to 20 fold by increasing membrane cholesterol levels. By using various cyclodextrin complexes and lipid vesicles we found that this effect on ABCG2 was selective for alterations in membrane cholesterol. Results of substrate stimulated ATPase assays confirmed this finding.

Vanadate- and inhibitor-sensitive membrane ATPase activity in ABC transporter expressing cell membrane preparations has been shown to correlate with the transport activity of these proteins [B. Sarkadi, L. Homolya, G. Szakacs, A. Varadi, Human multidrug resistance ABCB and ABCG transporters: participation in a chemoimmunity defense system, Physiol Rev 86 (2006) 1179-1236.].

Similar behaviour was found with BSEP, as shown herein. BSEP (ABCB11) is the major liver bile-salt transporter. It has been shown that inhibition of BSEP may impair bile acid transport into the bile, and thus may contribute to drug-induced hepatotoxicity.

This effect of membrane cholesterol was absent in the case of the R482G mutant variant of the transporter.

Based on these findings and the technical teaching provided herein, the skilled person is prompted and enabled to test further ABC transporters. The skilled person will readily decide whether a given further ABC transporter protein tested is a transporter protein having an increased substrate transport activity as compared to the substrate transport activity of said ABC transporter protein if present in the same type of insect cell membrane having a physiological cholesterol level, as taught herein.

Assay systems for testing ABC transporters, such as vesicular transport assays and substrate stimulated ATPase assays are disclosed herein together with methods for cholesterol loading methods. Many preferred technical details of such assays are well known in the art [see e.g. but not exclusively B. Sarkadi, E. M. Price, R. C. Boucher, U. A. Germann, G. A. Scarborough, Expression of the human multidrug resistance cDNA in insect cells generates a high activity drug-stimulated membrane ATPase, J Biol Chem 267 (1992) 4854-4858.; M. Muller, E. Bakos, E. Welker, A. Varadi, U. A. Germann, M. M. Gottesman, B. S. Morse, I. B. Roninson, B. Sarkadi, Altered drug-stimulated ATPase activity in mutants of the human multidrug resistance protein, J Biol Chem 271 (1996) 1877-1883; C. Ozvegy, A. Varadi, B. Sarkadi, Characterization of drug transport, ATP hydrolysis, and nucleotide trapping by the human ABCG2 multidrug transporter. Modulation of substrate specificity by a point mutation, J Biol Chem 277 (2002) 47980-47990, which are incorporated herein by reference].

In the description further guidance is provided as to the mode of action of cholesterol on ABC transporters. While this mechanism belongs to the realm of theory and it is not intended to limit the scope of invention thereby, the results discussed below can help the skilled person to find further ABC transporters which are useful in the insect cell preparations or the insect cell membrane preparations of the invention.

In particular, cholesterol loading mainly affected enzyme activity with relatively little effect on the affinity to ABCG2. Therefore, on vesicular transport data generated in the past using plasma membranes prepared from insect cells with the aim of identifying ABCG2 substrates as well as substrate specificities are not affected, but earlier ABCG2-ATPase data obtained in insect cell systems may have given false negatives especially for high affinity substrates. This support the notion that cholesterol loaded ABCG2-Sf9 membranes are the test systems of choice to study drug—ABCG2 interactions at high throughput.

We have not observed any signs of inhibition of ABCG2 transport exerted by cholesterol in our studies, questioning the substrate nature of cholesterol. Alternatively, cholesterol may act as an allosteric regulator for ABCG2-function. Further studies are required to elucidate the mechanism of cholesterol mediated potentiation of ABCG2-ATPase activity and vesicular transport. Moreover, membrane localization of ABCG2 was found to be unchanged in the course of these cholesterol modulating experiments.

Vanadate-dependent formation of a trapped nucleotide by ABCG2, reflecting the catalytic intermediate in ABC transporters in isolated Sf9 cell membrane preparations has also been studied [C. Ozvegy, A. Varadi, B. Sarkadi, Characterization of drug transport, ATP hydrolysis, and nucleotide trapping by the human ABCG2 multidrug transporter. Modulation of substrate specificity by a point mutation, J Biol Chem 277 (2002) 47980-47990]. In our present experiments we found that in cholesterol enriched Sf9 cell membranes transported substrates produced an increased rate of catalytic intermediate formation also in the wild-type ABCG2. This finding indicates that cholesterol increases the rate of the formation of a catalytic intermediate and enhances the drug substrate-dependent turnover of ABCG2.

In this study we observed that the effect of membrane cholesterol was specific for the wild-type ABCG2 protein, containing an Arg (R) at the proposed intracellular membrane region of the third transmembrane loop of the protein. Replacement of this Arg by Gly or Thr significantly alters the substrate specificity of ABCG2, and seems to removes its cholesterol modulation. Our present experiments indicate that these mutant ABCG2 variants may show a significantly higher transport activity only in the cholesterol-poor Sf9 cell membranes, and at increasing membrane cholesterol levels the wild-type protein may achieve a transport capacity approaching that in the mutant variants.

These findings exclude a non-specific stabilization or modulation of this protein by cholesterol, and suggest that cholesterol may interact with a region involved in the catalytic/transport region of ABCG2. Thus, this region may have a special role of this protein region both in the substrate recognition and cholesterol modulation of ABCG2.

Thus, in an embodiment of the invention the skilled person is advised to search for ABC transporters which are capable to interact with cholesterol at their region involved in catalysis and transport. Moreover, it is preferred if cholesterol increases turnover rate, i.e. increases enzymatic activity (optionally described by $V_{max}$) with relatively little effect on the substrate affinity to ABCG2 (optionally described by a little variance in $K_M$).

EXAMPLES

1. Experimental Procedures

Unless specifically stated otherwise, the following experimental procedures were applied.

Chemicals and Biochemicals: [$^3$H]-Methotrexate was purchased from Moravek Biochemicals (Brea, Calif., USA). [$^3$H]-estrone-3-sulfate and [$^3$H]-prazosin were purchased from Perkin Elmer/NEN (Boston, Mass., USA). Topotecan was purchased from LKT Laboratories (St. Paul, Minn., USA). The antibody against ABCG2 was purchased from Abcam (Cambridge, UK). Randomly methylated-β-cyclodextrin (RAMEB) and cholesterol complex of RAMEB [cholesterol@RAMEB (Piel et al. 2006), cholesterol content 4.74%] was provided by Cyclolab (Cyclodextrin Research & Development Laboratory) (Budapest, Hungary). Ko134 and Ko143 (Allen et al., 2002) were kind gifts of prof. G J Koomen (National Cancer Institute, Amsterdam). Other reagents were purchased from Sigma-Aldrich (St. Louis, Mo., USA) unless stated otherwise in the text.

Protein expression in insect cells: For Sf9 cell expression, cDNAs of human ABCG2 and its mutant variants were cloned into recombinant baculovirus transfer vectors, the insect cells were cultured, and infected with the baculoviruses as described in [C. Ozvegy-Laczka, G. Koblos, B. Sarkadi, A. Varadi, Single amino acid (482) variants of the ABCG2 multidrug transporter: major differences in transport capacity and substrate recognition, Biochim Biophys Acta 1668 (2005) 53-63]. Virus-infected Sf9 cells were harvested, cell membranes were isolated, and membrane protein concentrations were determined as described previously [C. Ozvegy, T. Litman, G. Szakacs, Z. Nagy, S. Bates, A. Varadi, B. Sarkadi, Functional characterization of the human multidrug transporter, ABCG2, expressed in insect cells, Biochem Biophys Res Commun 285 (2001) 111-117.; C. Ozvegy-Laczka, G. Koblos, B. Sarkadi, A. Varadi, Single amino acid (482) variants of the ABCG2 multidrug transporter: major differences in transport capacity and substrate recognition, Biochim Biophys Acta 1668 (2005) 53-63.; M. Muller, E. Bakos, E. Welker, A. Varadi, U. A. Germann, M. M. Gottesman, B. S. Morse, I. B. Roninson, B. Sarkadi, Altered drug-stimulated ATPase activity in mutants of the human multidrug resistance protein, J Biol Chem 271 (1996) 1877-1883.]

The level of ABCG2 expression was detected by immunoblotting, using the BXP-21 monoclonal antibody and the enhanced chemiluminescence technique (ECL, Amersham Biosciences). Quantitation of ABCG2 expression was achieved by densitometry of the immunoblots.

ABCG2 deglycosylation: Enzymatic deglycosylation was done using Peptide-N-Glycosidase F (Sigma, St. Louis, Mo.). One µl of the enzyme at 500 units/ml was added to 50 µl of membrane suspension (5 mg protein/ml) in TMEP (50 mM Tris, 50 mM mannitol, 2 mM EGTA, 8 µg/ml aprotinin, 10 µg/ml leupeptin, 50 µg/ml PMSF, 2 mM DTT, pH 7.0) vigorously mixed and incubated at 37° C. for 10 min. Deglycosylation was detected by Western blotting.

Cholesterol loading of Sf9 cells: Beta-methyl-cyclodextrin—cholesterol complex (cholesterol@RAMEB complex) was used for loading Sf9 cells with cholesterol (Cyclolab Ltd. Cat. Number: CY-9002.0). Any procedures known in the literature for cholesterol upload is applicable (see for example Sheets et al. J. Cell Biol. 1999, 145(4):877-87). The commonly used methodology was modified so that the cholesterol@RAMEB complex was added to the medium within 24 hours of the Sf9 cell infection. In a preferred variant of the method, e.g. at Bsep measurements, the commonly used methodology was modified so that the cholesterol-cyclodextrin was added to the infected cells during the membrane preparation, diluted in HBSS buffer.

Cholesterol loading of Sf9 vesicles: Beta-methyl-cyclodextrin—cholesterol complex (cholesterol@RAMEB complex) was used for loading Sf9 vesicles with cholesterol (Cyclolab Ltd. Cat. Number: CY-9002.0). The procedure was in accordance with the methodologies known in the literature for cholesterol upload (*Sheets* et al. J. Cell Biol. 1999, 145 (4):877-87). In short, the membranes were incubated for 30 minutes in the presence of cholesterol-cyclodextrin. The vesicles were separated from the medium containing the free cyclodextrin or cholesterol@RAMEB complex by "filter plating" or centrifugation. Such treated membranes were used for the ATPase and vesicular transport experiments. A part of the sample, and some untreated vesicles were reserved for the determination of cholesterol content using high performance liquid chromatography (HPLC).

In a variant of this method, used e.g. when mutants and wild type ABCG2 were compared, isolated membranes were prepared as described earlier but before the final centrifugation step the membranes were incubated for 20 min at 4° C. with 2-4 mM of various RAMEB cyclodextrin preparations (CD, C-CD or S-CD, obtained from Cyclolab). Cyclodextrin was eliminated in the course of the following high speed centrifugations. Membrane preparations were stored at −80° C. in aliquots and cholesterol content was estimated by the Amplex red kit, described above.

In the following experiments one of cholesterol loading methods described above was adopted.

Preparation of membrane vesicles: The membrane vesicles were prepared as described earlier (Sarkadi et al. JBC, 1992, Vol. 267, No. 7, pp 4854-8; Özvegy et al. BBRC, 2001, Vol. 285, pp. 111-117).

Human membrane vesicle preparations (ABCG2-M) as well as membrane vesicle preparations obtained from insect cells expressing ABCG2, (MXR-Sf9) were obtained from Solvo Biotechnology (Budapest, Hungary). Both membranes are overexpressing the wild type version of ABCG2. The insect membrane vesicle preparations were produced using recombinant baculoviruses encoding ABCG2 (Ozvegy et al., 2002). Sf9 cells were cultured and infected with recombinant baculovirus stocks as described earlier (Sarkadi et al., 1992). Purified membrane vesicles from baculovirus-infected Sf9 cells were prepared essentially as described previously (Sarkadi et al., 1992). Membrane protein content was determined using the BCA method (Pierce Biotechnology, Rockford, Ill., USA).

Cholesterol depletion: was preformed as known in the literature for inhibiting the activity of enzymes located in rafts and/or caveoli and of proteins involved in the signal transduction pathways (Keller and Simons J. Cell Biol. 1998, Vol. 140, No. 6, pp 1357-67; Lockwich et al. J. Biol. Chem. 2000, Vol. 275, No 16, pp 11934-42; Vainio et al. EMBO Rep. 2002, Vol. 391, Pt 3, pp 95-100.). Following treatment, cyclodextrin was removed as described above by filtration ("filter plate") or centrifugation. For both treated and untreated membranes the ATPase and vesicular transport activity was measured and the cholesterol content was determined.

Determination of the cholesterol content: The vesicles were suspended in a dilution containing 0.5% Na-cholate. The method is based on the enzymatic conversion of cholesterol where it is converted into cholest-4-en-3-one derivative by cholesterol oxidase, and then the oxidized residue is analyzed by HPLC. This conversion was necessary is essential as the HPLC signals of native cholesterol and cyclodextrin are interfering.

Measurement of transporter activity: The ATPase activity of transporters are measured based on their vanadate sensitivity as known in the literature (see Noe et al. Hepatology, 2001, Vol. 33, No. 5, pp 1223-31; Schmitt et al. J. Neural. Transm., in press; Özvegy C et al. "Functional characterization of the human multidrug transporter, ABCG2, expressed in insect cells" Biochem Biophys Res Commun. 2001 July 6; 285(1):111-7.; Sarkadi, B. et al. (1992) Expression of the human multidrug resistance cDNA in insect cells generates a high activity drug-stimulated membrane ATPase. J Biol Chem 267: 4854-4858.).

In case of ABCG2 the ATPase activity was measured in the presence of various activating agents (substrates) (sulfasalazin, topotecan, prazosin, mitoxantron and methotrexate) in a concentration dependently manner. The samples treated with cyclodextrin, or cholesterol@RAMEB complex was compared with untreated vesicles.

In case of Bsep the ATPase activity was measured in the presence of various activating agents (substrates) (taurochenodeoxycholate, taurocholate, glycocholate) concentration dependently. The samples treated with cholesterol@RAMEB complex were compared with untreated vesicles.

Briefly, as an example, membrane vesicles (20 µg/well) were incubated in ATPase assay buffer (10 mM MgCl2, 40 mM MOPS-Tris (pH 7.0), 50 mM KCl, 5 mM dithiothreitol, 0.1 mM EGTA, 4 mM sodium azide, 1 mM ouabain), 5 mM ATP and various concentrations of test drugs for 40 min at 37° C. ATPase activities were determined as the difference of inorganic phosphate liberation measured with and without the presence of 1.2 mM sodium orthovanadate (vanadate-sensitive ATPase activity). In further experiments, when combination of two substrates and/or a substrate and an inhibitor was tested, the PREDEASY ABCG2-ATPase Kit (SB-MXR-HAM-PREDEASY-ATPase Kit; Solvo Biotechnology, Szeged, Hungary) was used for the determination of ABCG2-ATPase activity according to the manufacturer's suggestions.

Measurement of the vesicular transport activity: The transport activity measurements were carried out with purified membrane vesicles containing ABCG2 or Bsep isolated from baculovirus infected Sf9 (*Spodoptera frugiperda*) cells or mammalian (ABCG2-M) cells. The membrane preparations contain 5-16% closed, inside-out oriented, membrane vesicles. The transporter pumps the molecules inside of these vesicles. The vesicles can be separated by rapidly filtrating of the membrane suspension through a glass filter or through a nitrocellulose membrane (using vacuum).

The quantitative determination of the transported molecule can be done in several ways, like: HPLC, LC/MS, but also fluorescent or radioactive labeling is also suitable. Tritium labeled substrates were used in the assays and the mode of detection was liquid-scintillation.

Measurement of the vesicular transport activity in case of ABCG2: More closely, as examples, inside-out membrane vesicles were incubated in the presence or absence of 4 mM ATP. For methotrexate vesicular transport the measurements were carried out in 7.5 mM MgCl2, 40 mM MOPS-Tris (pH 7.0), 70 mM KCl at 37° C. for 12 minutes. The transport was stopped by addition of cold wash buffer (40 mM MOPS-Tris (pH 7.0), 70 mM KCl).

For prazosin vesicular transport 10 mM Tris-HCl, (pH 7.4); 250 mM sucrose and 10 mM MgCl2 containing buffer was incubated at 37° C. for 20 minutes. The transport was stopped by addition of cold wash buffer (10 mM Tris-HCl, pH 7.4; 250 mM sucrose and 100 mM NaCl).

For estrone-3-sulfate vesicular transport 10 mM Tris-HCl, (pH 7.4), 250 mM sucrose, and 10 mM MgCl2 containing buffer were incubated at 32° C. for 1 min. The transport was stopped by addition of cold wash buffer (10 mM Tris-HCl, pH 7.4; 250 mM sucrose and 100 mM NaCl).

The incubation mix was then rapidly filtered through class B glass fiber filters (pore size, 0.1 µm). Filters were washed with 5×200 µl of ice cold wash buffer and radioactivity retained on the filter was measured by liquid scintillation counting. ATP-dependent transport was calculated by subtracting the values obtained in the absence of ATP from those in the presence of ATP.

Exemplary Assay Design and Main Steps for ABCG2

Prepare an appropriate concentration of membrane suspension in assay buffer; add the unlabeled and $^3$H-labeled substrates to the suspension. Distribute the suspension into 96 well microtiter plates.

Substrates:
$^3$H-Estrone-3-sulfate (Perkin Elmer, NET-203/9.25 MBq)
$^3$H-Methotrexate (Moravek, MT701)
Estrone-3-sulfate (Sigma, E0251)
Methotrexate Preincubate at incubation temperature; initiate the assay by adding MgATP
Incubate, stop the reaction by adding cold (4° C.) washing buffer
Filter on filter plates (Millipore: MSFBN6B10) and wash with washing buffer
Place a known quantity of membrane suspension droplet on an empty filter to determine the total counts per minute (cpm)
Dry the filter plate
Add the scintillation cocktail to the well to be measured
Measure with Liquid Scintillation Analyzer
Calculate the transport rate from the cpm obtained Measurement of the vesicular transport activity in case of Bsep: The transport activity measurements were carried out with purified membrane vesicles containing human, rat or mouse Bsep (ABCB11, sPgp) transporter isolated from baculovirus infected Sf9 (*Spodoptera frugiperda*)cells. The membrane preparations contain 5-16% closed, inside-out oriented, membrane vesicles. The transporter pumps the molecules inside of these vesicles. The vesicles can be separated by rapid filtration of the membrane suspension through a glass filter or through a nitrocellulose membrane (using vacuum).

The quantitative determination of the transported molecule can be done in several ways, like: HPLC, LC/MS, but also fluorescent or radioactive labeling is also suitable. Tritium labeled substrates were used in the assays and the mode of detection was liquid-scintillation.

Assay Design and Main Steps for Bsep

Prepare an appropriate concentration of membrane suspension in assay buffer; add the unlabeled and $^3$H-labeled substrates to the suspension. Distribute the suspension into 96 well microtiter plates.

Substrates:
$^3$H-Taurocholic acid (PerkinElmer, NET-322/9,25 MBq)
Taurocholic acid (Sigma, T0750)

Preincubate at incubation temperature; initiate the assay by adding MGATP
Incubate, stop the reaction by adding cold (4° C.) washing buffer
Filter on filter plates (Millipore: MSFBN6B10) and wash with washing buffer
Place a known quantity of membrane suspension droplet on an empty filter to determine the total counts per minute (cpm)

Dry the filter plate

Add the scintillation cocktail to the wells to be measured

Measure with Liquid Scintillation Analyzer

Calculate the transport rate from the cpm obtained

Determination of cholesterol content. The cholesterol content of the membranes was determined using the cholesterol oxidase method (Contreras et al., 1992). 10 μl of reaction mix (500 mM MgCl2, 500 mM Tris buffer, 10 mM DTT, 100 mg Triton X-100, pH 7.4) were mixed with 10 μl of cholesterol oxidase enzyme at 1 mg/ml (Roche Diagnostics, Basel, Switzerland) and 50 μl of membranes. The solution was incubated at 37° C. for 30 min. The reaction was stopped by adding 100 μl of a methanol/ethanol solution (50% (v/v)) and incubated at 0° C. for an additional 30 min. After 5 min centrifugation at 700g, 25 μl of the supernatant were analyzed by HPLC. For chromatographic separation an HPLC (1100 Series set, Agilent, Santa Clara, Calif., USA) and C18 reverse phase chromatographic column (3 μM, 100*2 mm Luna, Phenomenex, Torrance Calif., USA) were used. Analytes were separated using 1% (v/v) acetic acid/methanol as mobile phase at a flow rate of 0.3 ml/min. The oxidised cholesterol was detected using UV detector at 241 nm. To quantitate the amount of cholesterol, external cholesterol calibration standards were used.

Data analysis: The potencies of drugs to alter ATPase activity were obtained from plots of the rate of ATP hydrolysis as a function of logarithm of drug concentration by nonlinear regression of the general, sigmoid dose-response equation:

$$v = V_{min} + \frac{V_{max} - V_{min}}{1 + 10^{(logEC50 + [A])*Hillslope}} \quad \text{(Eq. 1)}$$

Where v=response (nmol Pi/min/mg), Vmin=minimal response, Vmax=maximal response, EC50=ligand concentration producing 50% of maximal response (efficacy), [A]=the actual test drug concentration and Hill-slope is parameter characterizing the degree of cooperativity. EC50 is defined according to the International Union of Pharmacology Committee (Neubig, R. R., Spedding, M., Kenakin, T. and Christopoulos, A. (2003) International Union of Pharmacology Committee on Receptor Nomenclature and Drug Classification. XXXVIII. Update on terms and symbols in quantitative pharmacology. Pharmacol Rev 55: 597-606.).

The transporters often have at least one high and one low affinity, inhibitory binding sites for the same drug. Therefore, bell shaped response curves were frequently obtained. For these types of curves an equation that is a combination of two sigmoid responses were used:

$$v = Dip + \frac{V_{min1} - Dip}{1 + 10^{(logEC50_1 - log[A])*Hillslope1}} + \frac{V_{min2} - Dip}{1 + 10^{(logEC50_2 - log[A])*Hillslope2}} \quad \text{(Eq. 2)}$$

Where v=response (nmol Pi/min/mg), Vmin1 and Vmin2=minimal responses, Dip=maximal response, EC501 and EC501=ligand concentrations producing 50% of maximal response (efficacy), [A]=the actual test drug concentration and Hillslope1 and Hillslope2 are the constant of cooperativity.

The Michaelis-Menten parameters of maximal velocity (Vmax) and drug affinity (Km) were obtained from plots of the ATPase activity as a function of test drug concentration by nonlinear regression of the following equation:

$$v = \frac{V_{max} \times [S]}{K_m + [S]} \quad \text{(Eq. 3)}$$

where v=enzyme activity (nmol Pi/min/mg), Vmax=maximal ATPase activity (nmol Pi/min/mg), Km=Michaelis-Menten constant for the tested substrate (nM) and [S] substrate concentration (nM). The equation 3 was used also for curve fitting on vesicular transport graphs.

As an example, for curve fitting, Vmax and Km slope calculations PRISM 3.0 software (Graphpad) can be used.

2. Experiments to Compare Insect Membranes and Human Membranes 2.1 Comparing ABCG2-A TPase Assays on sf9 and Human Membranes, in the Presence and Absence of Substrates, Optimization of Parameters The following results were obtained when comparing the Sf9 membrane preparations with the human membrane preparations. Both membranes displayed similar $K_M$ values for the vanadate sensitive basal ATPase activity with respect to ATP (2.0 mM and 2.2 mM respectively for ABCG2-Sf9 and ABCG2-M membranes), as well as for the ATP dependent vesicular [$^3$H]-methotrexate transport with respect to methotrexate (3.9 mM and 3.6 mM). In both cases the transport could be inhibited by 1 μM Ko143 selective ABCG2 inhibitor.

Figure 1:
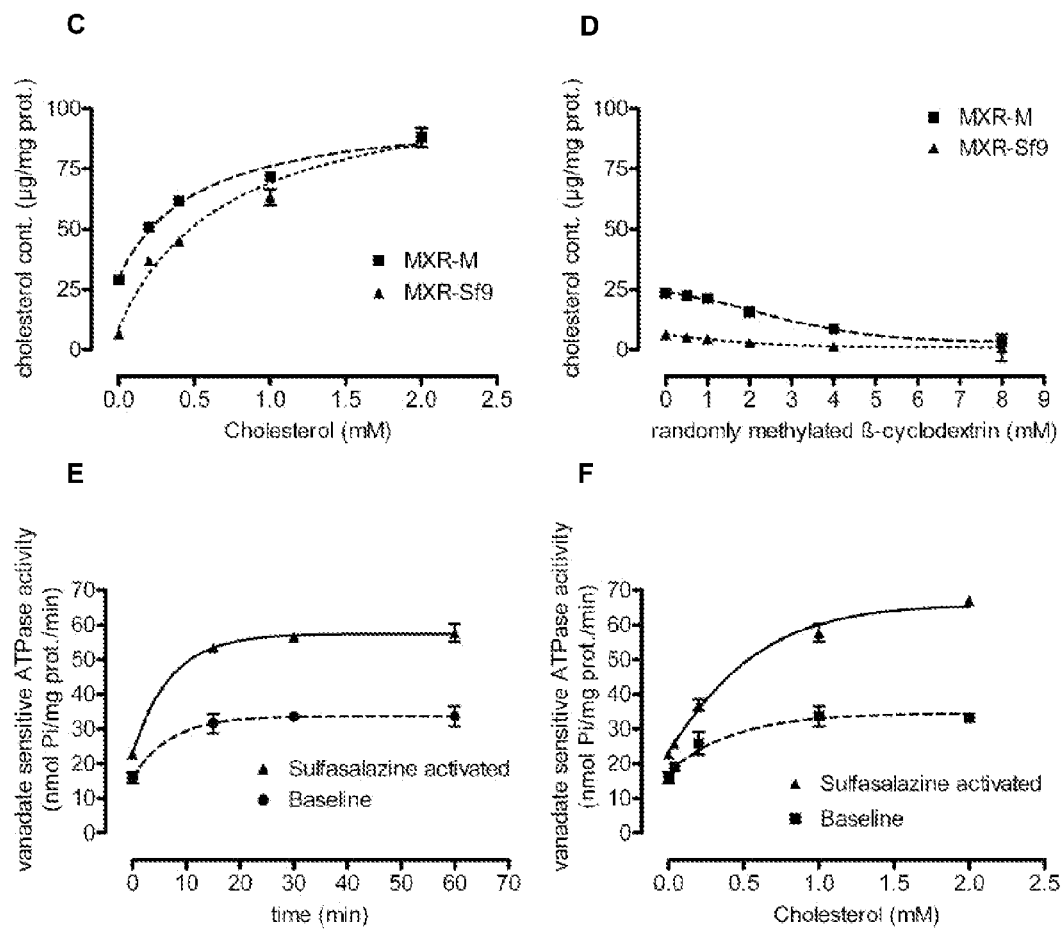
FIG. 1: Cholesterol content modulates vanadate sensitive ATPase activity in membrane preparations from ABCG2-Sf9 (from Sf9 cells) and ABCG2-M (from mammalian cells; on certain figures: MXR-M).

However, besides the similarities significant differences were observed. ABCG2 substrates like sulfasalazine, topotecan and prazosin only slightly influenced the ATPase activity of Sf9 membranes (sulfasalazine was a weak activator, whereas topotecan and prazosin were weak inhibitors; see FIG. 1A), while all three compounds significantly stimulated the ATPase activity of the human membranes (FIG. 1B). Thus Sf9 membrane preparations were not suitable to test these substrates.

It has been known that lipid composition of insect and mammalian membranes significantly differ, including cholesterol content [Gimpl, G., Klein, U., Reilander, H. and Fahrenholz, F. (1995) Expression of the human oxytocin receptor in baculovirus-infected insect cells: high-affinity binding is induced by a cholesterol-cyclodextrin complex. Biochemistry 34: 13794-13801]. The present inventors found that the cholesterol contents of the ABCG2-Sf9 and ABCG2-M vesicles containing ABCG2 protein were markedly different, with ABCG2-Sf9 displaying an about 4-5-fold lower cholesterol level (6.5 μg/mg protein vs 28.99 μg/mg protein (FIG. 1C) and 6.26 versus 23.68 (FIG. 1D). Cholesterol loading of both membranes using cholesterol@RAMEB treatment resulted in about a fifteen-fold increase of cholesterol content in ABCG2-Sf9 vesicles and three-fold increase in ABCG2-M vesicles yielding ~90 μg/mg protein final cholesterol content in both membranes (FIG. 1C). On the other hand, RAMEB treatment removed the cholesterol from both membranes very efficiently (FIG. 1D).

For further experiments cholesterol loading of ABCG2 expressing Sf9 membranes has been optimized for ATPase activity with respect to exposure time (FIG. 1E) and loading concentration of cholesterol (FIG. 1F). For experiments shown in FIG. 2 and FIG. 4 30 min and 1 mM cholesterol@RAMEB were chosen as optimal time and concentration. The membrane cholesterol content after treatment is around 60 μg/mg protein, about 2-fold greater than in the ABCG2-M membrane. We selected these values because under these conditions the membrane cholesterol content was relatively insensitive for either parameter (FIGS. 1E and F), therefore, it allowed for reproducible production of cholesterol loaded membranes.

For cholesterol depletion of ABCG2-M membranes a 30 min treatment using 8 mM RAMEB was selected yielding membrane preparations with an average cholesterol content of 3.5 μg/mg protein.

2.2 Comparison of the ATPase Activity of the Insect and Mammalian Cells in the Presence of Sulfasalazine After Cholesterol Loading or Depletion The vanadate sensitive ABCG2 (MXR) ATPase activity of untreated Sf9 vesicles increased from 20 nmol/Pi/mg prot/ min (FIG. 2. panel A, lower curve) by 5 nmol/Pi/mg prot/min in the presence of sulfasalazine. Following cholesterol loading the basal activity augmented to nearly 35 nmol/Pi/mg prot/min (FIG. 2 panel A, upper curve) which could be further activated to 58 nmol/Pi/mg prot/min (!) by sulfasalazine.

Figure 2:
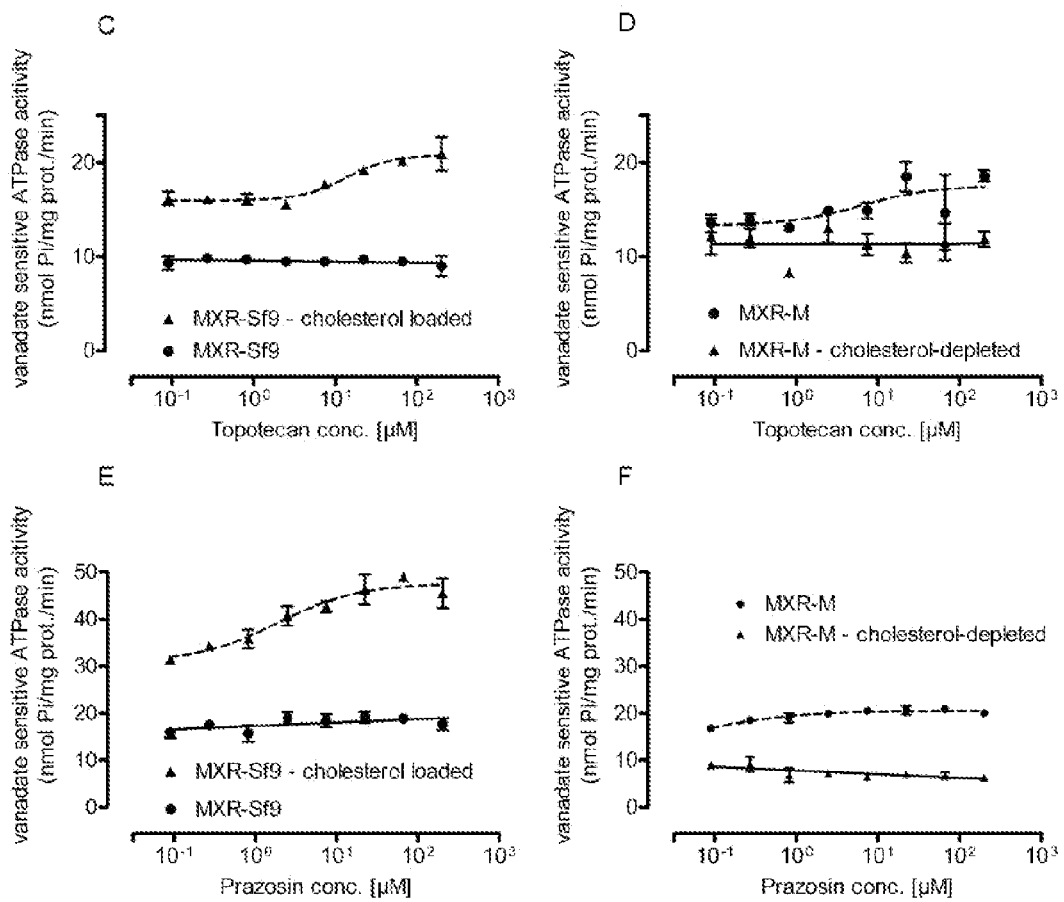
FIG. 2: Activation of cholesterol loaded Sf9 membranes containing ABCG2 ABCG2-Sf9 cells were loaded with cholesterol using cholesterol@RAMEB (1 mM total cholesterol) for 30 min at 37° C. Cholesterol depletion of ABCG2-M membranes were carried out at 37° C., for 30 min using 8 mM RAMEB.

The basal activity of vesicles prepared from mammalian cells is lower than 25 nmol/Pi/mg prot/min which could be increased to 40 nmol/Pi/mg prot/min by sulfasalazine, whereas cholesterol depletion of the cells significantly reduced both activities (FIG. 2 panel B, upper curve). Thus, Both the basal activity and the highest activity measured in the presence of sulfasalazine was increased in untreated cells, yet they were both significantly lower compared to the activities obtained with cholesterol loaded Sf9 membranes.

Similarly, topotecan and prazosin both significantly stimulated ABCG2-ATPase in cholesterol loaded ABCG2-Sf9 (FIGS. 2.C and E) and ABCG2-M membranes (FIGS. 2.D and F), while untreated ABCG2-Sf9 (FIGS. 2C and E) and cholesterol depleted ABCG2-M membranes (FIGS. 2D and F) were non-responsive. Kinetic data on the ABCG2-ATPase are summarized in Table 1. The data show good correlation between Vmax values obtained with the cholesterol loaded ABCG2-Sf9 membranes and ABCG2-M membranes. However, the Km values observed for the substrates were about 1.5-3.0 times greater with the cholesterol loaded ABCG2-Sf9 membranes.

TABLE 1

Comparison of ABCG2-ATPase kinetics of sulfasalazine, estrone-3-sulfate and topotecan obtained in cholesterol loaded ABCG2-Sf9 and native ABCG2-M membranes

| Test drug | ABCG2-Sf9 cholesterol loaded | | ABCG2-M | |
|---|---|---|---|---|
| | $V_{max}$* | $K_m$** | $V_{max}$* | $K_m$** |
| Sulfasalazine | 26.30 | 2.46 | 21.18 | 0.76 |
| Estrone-3-sulfate | 35.58 | 26.42 | 38.87 | 15.12 |
| Topotecan | 5.64 | 18.06 | 5.83 | 8.54 |

*nmol Pi/mg prot./min
**μM

Though there is a variance among the different membrane preparations, nonetheless within each a given membrane preparation a significant cholesterol dependence was always observed in each case.

3. Effect of Cholesterol Load on the Vesicular Transport Activity

Figure 3:
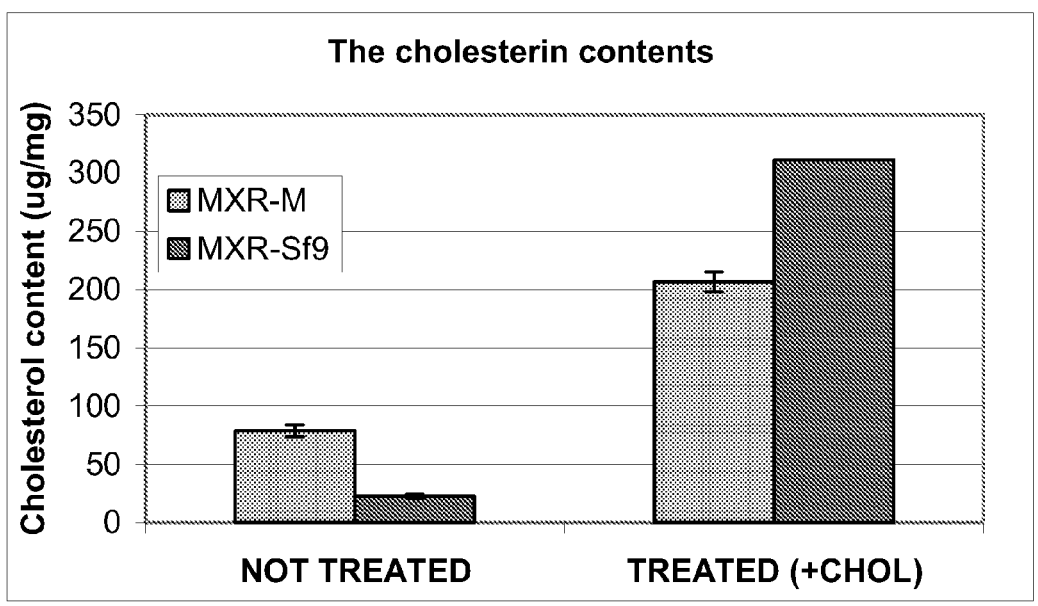
FIG. 3: Cholesterol dependence of vesicular transport using ABCG2 containing Sf9 membranes—FIG. 3.A: transport activity following and prior to cholesterol loading. Estron-3-sulfate concentration, 0.0465 μM, 25 μg/well protein content, 1 min incubation time. (Only tritium labeled estrone-3.sulfate was used when the experiment was set up, which explains the lower concentration compared to the experiment shown on FIG. 5).

With the help of radioisotope technology it can be shown that the increase of ATPase activity correlates with the actual transport of substrate molecules. Similarly to As in the ATPase assays "inside-out" membrane vesicles were used, and the assays were characterized by the ATP dependent uptake of the labeled substrates. As inSimilarly to the ATPase assays, the transport activity correlated with the cholesterol content of the vesicles (FIG. 3) when either E3S (Estrone-3-sulfate FIG. 3.A) or methotrexate was used as substrate (FIG. 3.B). As observed with the ATPase activity measurements, cholesterol increases the transport activity of vesicles prepared from Sf9 cells more than for those originating from mammalian membranes. In FIG. 3C the cholesterol content of vesicles used in the experiments is shown.

The substrate concentration dependence of the vesicular transport was investigated with methotrexate as shown on FIG. 4. The data was calculated based on the hypothesis that Michaelis-Menten kinetics is applicable. As seen in Table 2, while the $V_{max}$ increases by six-fold, the $K_M$ values only slightly changes.

TABLE 2

Effect of cholesterol loading on ABCG2 Sf9 cells; vesicular transport activity was measured vs. methotrexate concentration and kinetic parameters were calculated as descibed in the experimental part.

| | Untreated membranes ± S.D. | Cholesterol treated membranes ± S.D. |
|---|---|---|
| Vmax | 367.2 ± 21.91 | 2144 ± 29.92 |
| $K_M$ | 935.2 ± 142.2 | 1068 ± 36.46 |

Figure 5:
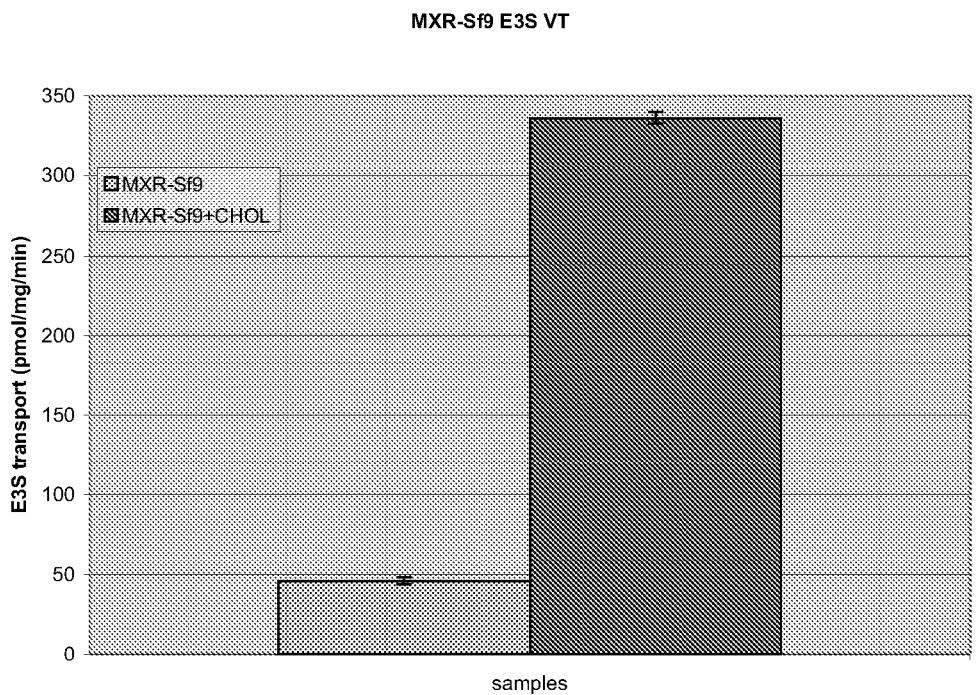
FIG. 5: Study of cholesterol loaded ABCG2-Sf9 membrane preparation. Comparison of estron-3-sulfate vesicular transport of cholesterol loaded and unloaded membranes (1 uM estron-3-sulfate, 25 µg/well protein content, 1 minute incubation time).

The estrone-3-sulfate transport of cholesterol treated and untreated Sf9 membranes is compared on FIG. 5. Experiments were carried out according to the standard E3S vesicular assay protocol used by Solvo as detailed in Example 1.

Figure 7:
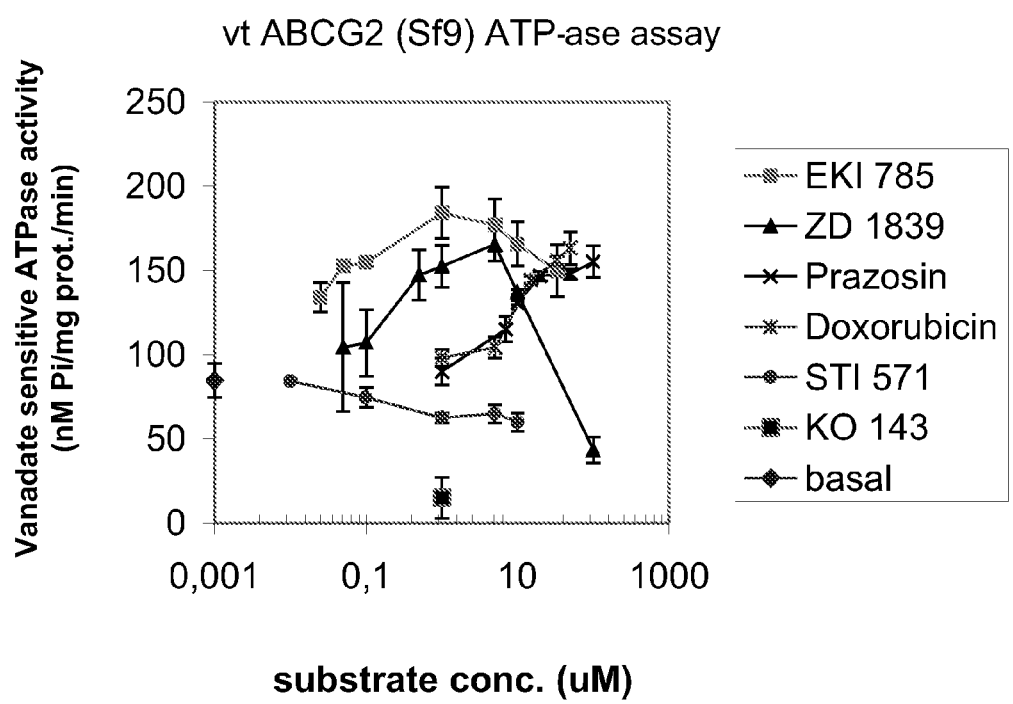
FIG. 7: The effect of different ABCG2 substrates and inhibitors on the ATPase activity of cholesterol preincubated Sf9 membranes (10 min, 1 mM cholesterol-cyclodextrin) as a function of concentration.

4. Measurement of ATPase Activity with Membranes that are Differently Loaded with Cholesterol by Different Methods In the ATPase assays, irrespective of the technology for cholesterol upload, all wild type (wt) ABCG2 expressing Sf9 membrane preparations displayed significantly higher substrate dependent activity changes (in some cases 100%) compared to that of control vesicles. The effects of substrates used in the study has already been shown previously with membrane preparations of mammalian origin, however, in the case of SfSF9 cells substrates induced only negligiable effects if any. According to the present knowledge cholesterol treatment does not modify the substrate specificity. In order to optimize the system, cholesterol loading of Sf9 membranes has been delivered via three routes:

a) Loading cholesterol directly prior to the ATPase assay. The membrane vesicles isolated were incubated in 1 mM cholesterol-cyclodextrin for 10 minutes at 37° C. (98.6 F), followed by the removal of unbound cholesterol@RAMEB complexes through centrifugation and then the ATPase assay was carried out (FIGS. 5 and 7, Table 3 below).

b) Loading living cells with cholesterol. 24 hours after Sf9 infection with the baculovirus the cholesterol@RAMEB complex was added to the medium at a given concentration and was cultured for an additional 48 hours. Membrane was prepared from these treated cells (FIG. 8).

c) Loading cholesterol during membrane preparation. Following homogenization and prior to ultracentrifugation the step of a cholesterol loading step was carried out is inserted, when the preparation is treated with 0.5-2 mM cholesterol-cyclodextrin for 20 minutes at +4° C. (39.2 F). This method proved to be the most effective, with the highest cholesterol load of membranes, while the size and quality of vesicles remained unchanged (FIG. 9).

The result of each cholesterol loading type is shortly described below.

Method a)

Figure 6:
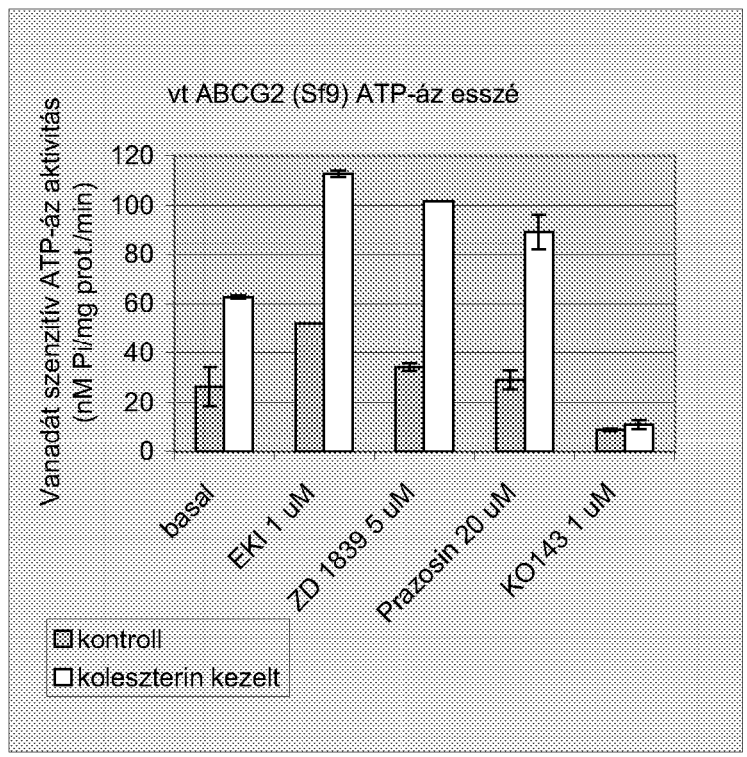
FIG. 6: Change of vanadate sensitive ATPase activity of wt (wild type) ABCG2 containing Sf9 membrane preparation as a result of 10 minutes preincubation with 1 mM cholesterol-cyclodextrin. The basal activity is the activity measured without substrates. In the presence of Ko143, a specific ABCG2 inhibitor activity nearly no activity can be detected. Three different substrates in the given concentrations were applied to investigate the effect of cholesterol (EKI, ZD1839, Prazosin).

The effect of cholesterol pre-incubation on wt ABCG2 containing Sf9 membrane preparations is shown on FIG. 6.

The relatively high basal ATPase activity of Sf9 membrane preparations increases as a result of cholesterol treatment. In the presence of Ko143, a specific ABCG2 inhibitor the effect is negligible and is not modified by cholesterol. For the three substrates (EKI, ZD 1839, prazosin) investigated cholesterol treatment caused a very significant ATPase activity increase, in contrast to control membranes where the effect was insignificant.

The table below summarizes the effect of investigated ABCG2 substrates that were effective in the ATPase assays with wt ABCG2 cholesterol treated membranes (according to item a). No effect was observed for the ** labeled substrates when the membrane preparation were not treated with cholesterol. Verapamil, mitoxantrone and rhodamine did not display any effect even with cholesterol treated membranes either in the ATPase assay.

TABLE 3

| Compound | Concentration | Level of stimulation (vanadate sensitive ATPase activity in % (the number of independent experiments are given in brackets) |
|---|---|---|
| EKI 785 | 1 uM | 100 ± 15 (7) |
| ZD 1839 | 5 uM | 73 ± 19 (3) |
| Prazosin** | 20 uM | 79 ± 12 (2) |
| Doxorubicin** | 50 uM | 83 ± 18 (3) |
| Sulfasalazin | 20 uM | 71% (3) |
| Topotecan | 200 uM | 31% (3) (can not be activated without cholesterol loading) |

| | Concentration | Level of inhibition (vanadate sensitive ATPase activity in % (number of experiments) |
|---|---|---|
| STI | 1 uM | 26 ± 4 (2) |
| FTC | 7 uM* | 45 (1) |
| KO 143 | 1 uM | 85 ± 7 (5) |

FIG. 7 depicts illustrates the concentration dependent stimulating and inhibitory effects of certain important ABCG2 substrates and inhibitors exhibited on the ATPase activity of Sf9 membranes pre-incubated with cholesterol. The results confirm that the effective concentration of activators and inhibitors are similar to that applied for mammalian membranes.

Method b)

The cholesterol load of living cells during the baculovirus infection of Sf9 cells compared to the pre-incubation method resulted in a lower, but still detectable effect. However, the use of this method is limited by the fact that the transporter expression decreases already at 1 mM cholesterol@RAMEB complex the transporter expression decreases, moreover, above this concentration it the complex has toxic effects. The cholesterol content is much lower in the final vesicles than if method c) is applied. FIG. 8. shows the result of a representative experiment.

Method c)

FIG. 9 shows the efficiency of cholesterol load when executed during the membrane preparation process according to method c). Similar results were obtained with other independent preparations. The bBasal activities for the given loading concentrations does not change vary, yet,whereas the maximal effect of the substrates is in the similar range as was for the vesicles loaded according to method a). According to the present results using 2 mM cholesterol-cyclodextrin for cholesterol load is a preferred in this embodiment of cholesterol loading the invention. In the a highly preferable variant of this embodiment of the invention the membrane preparation is incubated in a HBBS (pH 7.4) medium containing 0.55 mM cholesterol@RAMEB complex for 30 min, at 37° C. (98.6 F).

It must be noted that the vanadate sensitive ATPase activity, in the presence of the substrate is higher even at low ATP concentrations (0.2-0.4 mM) for cholesterol loaded membranes when EKI is the a substrate.

5. Comparison Effect of Cholesterol Loading on ABCG2 Mutants

In this set of experiment a systematic comparison of wild type ABCG2 its mutants has been carried out.

5.1. Experiments with Isolated Sf9 Cell Membranes

In order to explore the molecular details of the cholesterol effects observed in intact cells, ABCG2 and its R482G, R482T mutant variants were expressed in Sf9 cells. These cells were engineered to express high amounts of the human ABCG2 variants, at about equal transporter protein levels [Ozvegy-Laczka et al, Single amino acid (482) variants of the ABCG2 multidrug transporter: major differences in transport capacity and substrate recognition, Biochim Biophys Acta 1668 (2005) 53-63]. Moreover, in isolated membranes of Sf9 cells both direct vesicular transport, drug-stimulated ATPase activity and catalytic intermediate formation (nucleotide trapping) could be examined [Ozvegy et al., Characterization of drug transport, ATP hydrolysis, and nucleotide trapping by the human ABCG2 multidrug transporter. Modulation of substrate specificity by a point mutation, J Biol Chem 277 (2002) 47980-47990]. We have also studied in the same system the effects of cholesterol on the human MDR1 protein, expressed as described earlier [Sarkadi et al. Expression of the human multidrug resistance cDNA in insect cells generates a high activity drug-stimulated membrane ATPase, J Biol Chem 267 (1992) 4854-4858].

For cholesterol loading of Sf9 cell membranes, which contain relatively low levels of endogenous cholesterol, we applied a short preincubation of the membranes at 4° C. with cholesterol-beta cyclodextrin (C-CD, cholesterol@RAMEB), followed by a removal of this agent during the further centrifugation steps. The original membrane cholesterol content in our Sf9 cell membrane preparations was between 5-8 µg/mg membrane protein, and with 1-5 mM C-CD preincubation this cholesterol content could be gradually increased up to 60-80 µg cholesterol/mg membrane protein.

Vesicular transport studies: In these experiments we carried out direct, ATP-dependent substrate transport measurements by using isolated inside-out membrane vesicles of ABCG2-expressing Sf9 cells.

Figure 10:
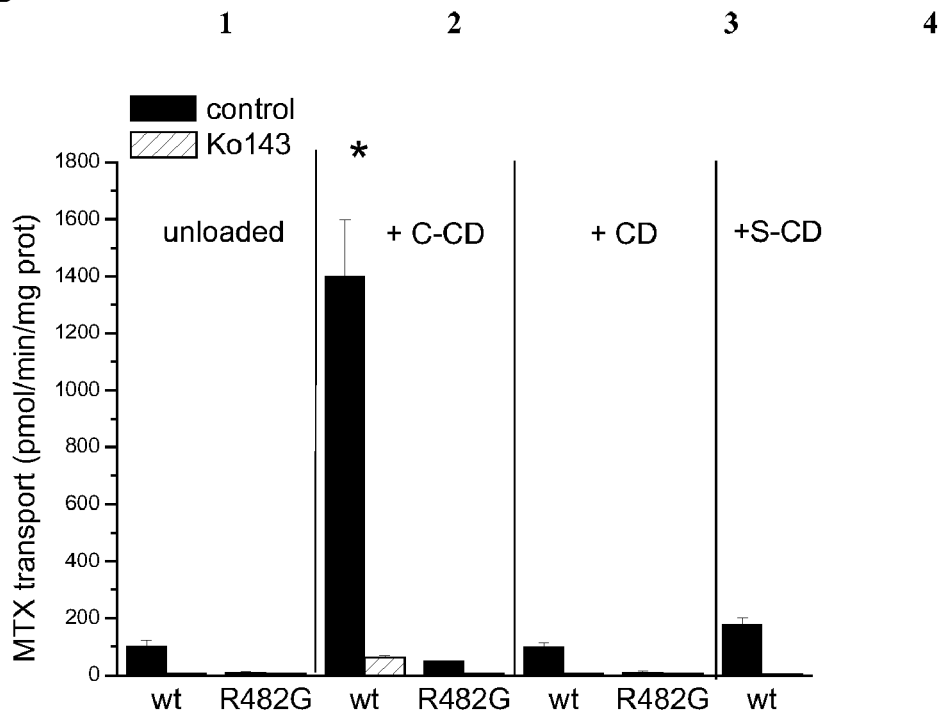
FIG. 10: Effect of cholesterol or sitosterol loading on the ATP-dependent transport of MTX in inside-out Sf9 membrane vesicles. MTX uptake was measured at 100 µM MTX concentration for 5 min at 37° C. in membrane vesicles containing the human wild-type ABCG2 (WT), or R482G-ABCG2 (G) transporter.

FIG. 10 demonstrates the effect of membrane cholesterol loading on the methotrexate (MTX) transport activity of the human ABCG2 protein in these membrane vesicles. Loading of the membranes with cholesterol (C-CD) greatly increased the transport activity of the wild-type ABCG2, to yield a 15-20 fold increase when the initial membrane cholesterol was elevated to 65 µg cholesterol/mg membrane protein. We found a similar large increase in the ABCG2-dependent uptake of estradiol beta-17-glucuronide (ESG—see below), and of estrone 3-sulfate (E3S—not shown) in the Sf9 membrane vesicles after cholesterol loading. We found that pretreatment with free cyclodextrin (CD) did not significantly affect either the MTX (see FIG. 10), ESG or E3G transport activity of the human ABCG2 protein. Also, when we applied sitosterol (S) loaded CD (FIG. 10—part 4), or phosphatidyl choline vesicles in a preincubation (not shown), we found no effect on the ABCG2-dependent transport activity. Ko143, a specific inhibitor of ABCG2, abolished substrate transport both in the control and cholesterol-loaded membrane vesicles.

The R482G or R482T variants of ABCG2 have significantly different substrate handling properties than the wild-type protein. These mutant variants transport certain negatively charged compounds, e.g. MTX, ESG or E3S only with a very low activity. As shown in FIG. 10, MTX transport by the ABCG2-R482G variant was very low both in the control and in the cholesterol-loaded Sf9 membrane vesicles. Similarly, the MTX transport rate by the ABCG2-R482T variant was below 50 pmoles/mg membrane protein/min, irrespective of the membrane cholesterol content. We found a similar lack of significant ESG and E3S transport by the R482G and R482T variants, irrespective of the cholesterol content of the membrane vesicles (not shown).

In the transport experiments documented herein, cholesterol loading of the vesicles before the transport experiment did not affect, while cholesterol loading during membrane preparation somewhat (by 20-30%) decreased the relative membrane vesicular content, measured by endogenous calcium transport activity. Therefore any increase in vesicular transport activity of ABCG2 is probably even underestimated (we did not perform a systematic correction based on this estimation).

All these experiments suggest that the C-CD effect was specific for the wild-type ABCG2, and depletion of other lipid constituents of the Sf9 cell membrane (e.g. by unloaded CD), a non-specific increase in membrane lipids, or non-specific permeability changes (e.g. by Sitosterol-CD, i.e. S-CD or PC vesicles) could not be accounted for the observed effects.

5.2 Effect of Cholesterol Loading on the Kinetic Parameters of MTX and ESG Transport by ABCG2 and its Mutants In the following experiments we examined how cholesterol loading affected the kinetic parameters of MTX and ESG transport by ABCG2. FIG. 11.A shows the MTX concentration dependence of the ABCG2-dependent MTX uptake in control, and cholesterol-loaded Sf9 membrane vesicles, respectively. In the original, untreated Sf9 cell membrane vesicles (containing 6-8 µg cholesterol/mg membrane protein) the rate of MTX uptake was low, with an apparent Vmax of about 0.5 nmol MTX/mg membrane protein/min. In contrast, in the C-CD pretreated vesicles (in this experiment containing 55 µg cholesterol/mg membrane protein), MTX uptake had an estimated $V_{max}$ of about 10 nmol MTX/mg membrane protein/min. The apparent Km of MTX uptake was about 0.5 mM in both cases, but the proper determination of the Km and Vmax values in these experiments was hindered by the low solubility of MTX at higher than 3 mM concentrations. FIG. 11.A also documents that the R482G variant of ABCG2 had a very low MTX transport activity, irrespective of the MTX concentrations examined.

When we examined the effect of membrane cholesterol on the ATP concentration dependence of the MTX uptake in the ABCG2-containing Sf9 membrane vesicles we found that, irrespective of the membrane cholesterol content, MTX transport had a saturable ATP-dependence, with an apparent Km of 0.6-0.8 mM ATP and a maximum transport rate at about 5 mM ATP. These values are in agreement with the data in the literature for the ATP-dependence of vesicular transport by ABCG2. Again, neither the R482G, nor the R482T variants showed any MTX transport activity, irrespective of the ATP concentration or the cholesterol content of the Sf9 cell membrane vesicles.

In the following experiments we examined the ESG concentration dependence of ATP-dependent ESG uptake in Sf9 membrane vesicles (FIG. 11.B). Similarly to that seen for MTX, in the cholesterol-loaded vesicles this transport showed simple saturation kinetics, with an apparent Vmax of 700 pmol ESG/mg membrane protein/min, while the apparent Km for ESG was about 45 µM. In the control Sf9 membrane vesicles ESG uptake was too low for a proper estimation of Km. An apparent saturation of this uptake was also achieved above 100 µM ESG, with an apparent Vmax of less than 50 pmol ESG/mg membrane protein/min.

These experiments suggest that modulation of the MTX and ESG transport by membrane cholesterol has a predominant effect on the Vmax, that is increasing the substrate transport capacity of this active transporter. Cholesterol may also slightly modulate the substrate affinity and the transporter/substrate interactions, but we need further studies in this respect.

FIG. 11.C demonstrates the stimulation of the MTX and ESG transport in inside-out Sf9 cell membrane vesicles by different membrane cholesterol levels. The effect of cholesterol on the vesicular transport was measured at MTX and ESG concentrations (50 µM MTX and 25 µM ESG, respectively) below saturating values. In these experiments pooled membrane preparations, containing the same amount of human ABCG2, but loaded to different cholesterol levels, were applied. Although a slight difference in these activation curves may be observed, the effect of cholesterol on both ABCG2-dependent MTX and ESG transport was maximum above 55 µg cholesterol/mg membrane protein. Thus cholesterol modulation of ABCG2 transport activity was the most pronounced in the range of physiological cholesterol levels in various mammalian cellular membranes.

As a summary, membrane cholesterol greatly and selectively increased substrate transport by the wild-type ABCG2, while we found no major changes by cholesterol in the substrate handling properties of the mutant ABCG2 protein variants.

5.3. Membrane ATPase Measurements

In the following experiments we examined the effect of cholesterol loading on the membrane ATPase activity of the MDR1 and the ABCG2 proteins. Vanadate-sensitive membrane ATPase activity, selectively blocked by a specific inhibitor, reflects the transport activity of a number of the ABC multidrug transporters (Gottesman et al., Multidrug resistance in cancer: role of ATP-dependent transporters, Nat Rev Cancer 2 (2002) 48-58; Sarkadi et al., Human multidrug resistance ABCB and ABCG transporters: participation in a chemoimmunity defense system, Physiol Rev 86 (2006) 1179-1236; Sarkadi et al., Expression of the human multidrug resistance cDNA in insect cells generates a high activity drug-stimulated membrane ATPase, J Biol Chem 267 (1992) 4854-4858]. As reported earlier, the ABCG2-ATPase activity can be specifically inhibited by Fumitremorgin C or its analog, Ko143. This "basal" ABCG2-ATPase activity is relatively high in isolated Sf9 cell membrane vesicles, but a significant substrate-activation could not be detected in the case of the wild-type protein in the Sf9 cell membrane preparations.

FIG. 12.A shows the vanadate-sensitive ATPase activity of the wild-type ABCG2 as well as the R482G and the R482T variants, both in the absence and presence of two potential transported substrates. In these studies we selected prazosin, and the EKI-785 tyrosine kinase inhibitor (EKI), as these compounds were shown to be substrates both for the wild-type, as well as the R482G or R482T variants of ABCG2 [C. Ozvegy-Laczka, G. Koblos, B. Sarkadi, A. Varadi, Single amino acid (482) variants of the ABCG2 multidrug transporter: major differences in transport capacity and substrate recognition, Biochim Biophys Acta 1668 (2005) 53-63].

In FIG. 12.A we document the respective ATPase activities measured at two different membrane cholesterol levels, that is in the control (6-8 µg cholesterol/mg membrane protein) and cholesterol-loaded (50-65 µg cholesterol/mg membrane protein) Sf9 cell membranes, respectively. Ko143 was shown to fully and selectively inhibit the transport activities in all these ABCG2 variants, and the level of the endogenous vanadate-sensitive ATPase activity in the control Sf9 cell membranes was in the range of that measured in the presence of Ko143 in the ABCG2 expressing membranes (about 8-10 nmoles/mg membrane protein/min). These data indicate that the Ko143 sensitive fraction of the membrane ATPase activity closely correlates with the activity of the ABCG2 protein.

As documented in FIG. 12.A, cholesterol loading of the Sf9 cell membranes did not significantly affect, or only slightly increased the basal ATPase activity of all the three ABCG2 variants, and did not affect the low background ATPase activity measured in the presence of Ko143. However, cholesterol loading greatly increased the drug-stimulated ATPase activity of the wild-type ABCG2 in the presence of both substrates, while had no such effect in the case of the R482G or R482T mutant variants. Thus, the effect of cholesterol on the drug-stimulated ATPase activity is in close correlation with the observed alterations in the direct vesicular substrate transport, while the basal ATPase activity may not be directly related to this transport.

In the following experiments we have examined the effects of several transported substrates on the ABCG2-ATPase activity (the Ko143-sensitive fraction) in isolated Sf9 cell membranes in a concentration range of 0.1-50 micromolar. According to our earlier studies, in this system we did not observe, or obtained only a minor stimulation of the ABCG2-ATPase activity by the compounds examined. As shown in FIGS. 12.B and C, the compounds already indicated to be transported substrates of ABCG2, that is the tyrosine kinase inhibitor Iressa (Gefitinib), the widely applied topotecan, the irinotecan metabolite SN38, the experimental anticancer agent flavopiridol, and the flavonoid compound quercetin, all produced a major stimulation of the ABCG2-ATPase activity in the cholesterol-loaded Sf9 cell membranes (FIG. 12.B), while there was only a small stimulation in the control membranes (FIG. 12.C). In the case of quercetin and some tyrosine kinase inhibitors this stimulation was observed already in sub-micromolar concentrations and produced very high maximum ATPase activity levels. These data show that in cholesterol-loaded Sf9 membranes ABCG2 substrate screening, based on measuring Ko143-sensitive ATPase activity, can be efficiently and reliably performed.

6. Nucleotide Trapping Measurements

In order to explore the molecular mechanism of the cholesterol effect on human ABCG2, we examined the vanadate-sensitive nucleotide trapping in the control and the cholesterol-loaded isolated Sf9 cell membranes, respectively. Most active ABC transporters form a catalytic intermediate, stabilized by the presence of vanadate, which can be visualized through UV-dependent photo-cross-linking and covalent labeling by alpha $^{32}$P-8-azido-ATP [Gottesman et al, Multidrug resistance in cancer: role of ATP-dependent transporters, Nat Rev Cancer 2 (2002) 48-58]. As we documented earlier, in the case of ABCG2 this experiment requires the use of Co-alpha $^{32}$P-8-azido-ATP, and nucleotide trapping is entirely vanadate-dependent.

In our earlier nucleotide trapping experiments, carried out in human ABCG2-containing Sf9 cell membranes, we found that in the case of wild-type ABCG2 the addition of drugs, e.g. prazosin, did not increase, but rather slightly decreased the formation of this intermediate (see Ozvegy et al. Characterization of drug transport, ATP hydrolysis, and nucleotide trapping by the human ABCG2 multidrug transporter. Modulation of substrate specificity by a point mutation, J Biol Chem 277 (2002) 47980-47990]. In contrast, nucleotide trapping in the ABCG2-R482G variant was significantly increased by transported substrates.

In the current study we repeated these experiments in Sf9 cell membranes, expressing ABCG2, either without or with cholesterol preloading. As shown in FIG. 13, in the control Sf9 cell membranes vanadate-dependent nucleotide trapping was well measurable, but the addition of prazosin or EKI only slightly decreased the formation of this intermediate. When calculating the average values in three independent experiments, corrected by the immunoblot loading control of ABCG2, the relative ABCG2 labeling was decreased to 45% by prazosin and to 55% by EKI. Cholesterol loading did not alter the basic level of ABCG2-nucleotide trapping (the mean relative value of ABCG2 labeling was 105%). However, the addition of prazosin (a relative increase to 125%), or even more significantly, of EKI (an increase to 180%), stimulated nucleotide trapping in the cholesterol-loaded membranes, in contrast to the strong decrease produced by these drugs in the unloaded control membranes. Similar results were obtained at two different time-points (2 min and 5 min) in these nucleotide trapping studies. In all cases the addition of Ko143 eliminated ABCG2-dependent nucleotide trapping.

In the case of the ABCG2-R482G mutant variant, prazosin and EKI stimulation of nucleotide trapping was already present in the control membranes, and in this case we did not find any significant difference by cholesterol enrichment of the Sf9 cell membranes in the present study (data not shown).

These experiments indicate a significant effect of membrane cholesterol on the rate of nucleotide trapping by the human ABCG2 protein. In correlation with the observed acceleration of direct vesicular substrate transport, and the appearance of drug-stimulated ATPase activity, cholesterol loading was found to promote the drug stimulation of the formation of the catalytic intermediate, indicating a cholesterol stimulation of the turnover of the wild-type transporter.

6. Experiments to Compare the Cholesterol-loaded and Not-loaded Sf9 Membranes Containing Bsep Transporter 6.1 Comparison of the ATPase Activity of the Cholesterol Loaded and Not-loaded MouseBsep Membrane The vanadate sensitive basal ATPase activity of untreated mouseBsep vesicles increased from 37 nmol Pi/mg prot/min to 64 nmol Pi/mg prot/min in the presence of taurochenodeoxycholate (FIG. 14.A). Following cholesterol loading, the basal activity decreased to 4.7 nmol Pi/mg prot/min that could be activated to 39 nmol Pi/mg prot/min by taurochenodeoxycholate (FIG. 14.B). This method resulted better signal to noise ratio for mouseBsep ATPase assay compared to the un-loaded membranes which is more suitable to screen compounds.

Significant differences were observed in the activation by taurocholate and glycocholate using treated and untreated mouseBsep-Sf9 vesicles (FIG. 14.A, B).

6.2 Effect of Cholesterol Loading on the Vesicular Transport Activity of Human/Mouse/Rat Bsep Transporter Similarly to the ATPase assays, "inside-out" membrane vesicles were used and the assays were characterized by the ATP dependent uptake of the labeled substrates. Cholesterol increases the taurocholate transport activity of vesicles prepared from Sf9 cells which contain rat/human/mouse Bsep transporter (FIG. 15.A, B, C). This effect was observed in the highest degree in case of ratBsep transport activity (FIG. 15.A.). The $K_M$ and Vmax values were calculated using the hypothesis that Michaelis-Menten kinetics are applicable. As seen in Table 3, while the Vmax values increase significantly, the $K_M$ values change only slightly.

TABLE 3

Calculated $K_M$ and Vmax values using Michaelis-Menten equation

| Best-fit values | ratBsep-Sf9 + Chol | ratBsep-Sf9 − CTRL | humanBSEP-Sf9 − CTRL | humanBSEP-Sf9 + Chol | mouseBsep-Sf9 − CTRL | mouseBsep-Sf9 + Chol |
|---|---|---|---|---|---|---|
| $V_{MAX}$ (pmol TC/mg prot/min) | 121.3 | 14.54 | 169.4 | 323 | 1199 | 1843 |
| $K_M$ (μM) | 19.55 | 2.203 | 15.03 | 17.04 | 6.798 | 7.608 |

APPLICATIONS, ADVANTAGES

The present inventors have revealed that the phenomenon is suitable to set up assay systems with a preferred embodiment compared to that known by the art.

An important result of the present invention is that by using cholesterol preloaded membranes this technology allows the screening of a wide variety of substrate molecules by measuring ABCG2-ATPase activity.

Indeed, cholesterol loading specifically improved the rate of drug stimulated ATPase and maximal velocity of transport for the substrates studied in vesicular transport experiments Cholesterol loading of insect cell membranes makes their ATPase and transport properties similar to the mammalian membranes that contain high levels of endogenous cholesterol. Therefore, cholesterol loaded ABC-transporter, e.g. BSEP or ABCG2 overexpressing insect cell membranes are suitable models to study transporter function.

Abbreviations: ABC transporters: ATP binding cassette transporters; ABCP: placenta specific ABC transporter; ADME: Absorption Distribution Metabolism Excretion; BCRP: breast cancer resistance protein; CD: cyclodextrin, C-CD: cyclodextrin loaded with cholesterol, S-CD: cyclodextrin loaded with sitosterol, EKI: EKI-785 tyrosine kinase inhibitor, ESG: estradiol 17-beta glucuronide, E3S: estrone 3-sulfate, MDR1: Multi Multidrug Resistance protein 1; MRP1: multidrug resistance-associated protein 1; MTX: methotrexate, MXR, mitoxantrone resistance-associated protein; P-gp: P-glycoprotein; PheA: Pheophorbide A, PNGase F: Peptide-N-Glycosidase F; RAMEB: randomly methylated β-cyclodextrin, Sf9 cells: *Spodoptera frugiperda* ovarian cells.

The invention claimed is:

1. A cholesterol loaded insect cell membrane preparation or insect cell preparation comprising an increased membrane cholesterol level as compared to the physiological cholesterol level of the same type of insect cell membrane, said insect cell membrane preparation or insect cell preparation comprising an ATP binding cassette (ABC) transporter protein having an increased substrate transport activity as compared to the substrate transport activity of said ABC transporter protein if present in the same type of insect cell membrane having a physiological cholesterol level,
    wherein the ABC transporter protein is ABCG2 or ABCB11.

2. The preparation of claim 1 wherein the cholesterol level is calculated as the cholesterol content relative to the total protein content and is
    at least 25 μg/mg total protein or
    at least 2 times that of the physiological cholesterol level present in the same type of insect cell membrane.

3. The preparation of claim 1 wherein the substrate transport activity of the ABC transporter protein is tested by
    a) a vesicular transport assay or
    b) a substrate stimulated ATP-ase assay.

4. The preparation of claim 3 wherein the substrate transport activity of the ABC transporter protein is at least 1.5 times higher than the substrate transport activity of said ABC transporter protein if present in a control insect cell preparation or insect cell membrane preparation of the same type having a physiological cholesterol level present in the same type of insect cell membrane.

5. The preparation of claim 1 wherein the ABC transporter protein is ABCG2.

6. The preparation of claim 1 wherein the ABC transporter protein is ABCB11.

7. A reagent kit for assessing activity of an ABC transporter protein, said kit comprising
    the cholesterol loaded insect cell membrane preparation or insect cell preparation of claim 1, or
    means for expressing said ABC transporter in insect cells and means for loading the insect cells with cholesterol or a cholesterol analogue, and optionally means for preparing a membrane preparation from the insect cells, and
    if desired, any of the following: substrates of the ABC transporter protein, ATP, cholesterol or cholesterol analogues, buffers, reagents, inhibitors or activators of the ABC transporter protein,
    wherein the ABC transporter protein is ABCG2 or ABCB11.

8. A method for manufacturing an insect cell preparation or an insect cell membrane preparation comprising an ABC transporter protein having increased substrate transport activity, for use in an ABC transporter protein assay,
    wherein said method comprises
        providing an ABC transporter protein having substrate transport activity in an insect cell preparation or an insect cell membrane preparation,
        loading the insect cell preparation or the insect cell membrane preparation with cholesterol thereby increasing cholesterol level of the insect cell preparation or the insect cell membrane preparation,
        testing the obtained cholesterol loaded insect cell preparation or insect cell membrane preparation for increased substrate transport activity of the ABC transporter protein as compared to the same activity in a control insect cell preparation or insect cell membrane preparation having a physiological cholesterol level present in the same type of insect cell membrane
    wherein the ABC transporter protein is ABCG2 or ABCB11.

9. The method of claim 8 wherein
    the cell membrane preparation is prepared from insect cells comprising the ABC transporter protein and
    the cell membrane preparation is incubated with a complex of cyclodextrin and the cholesterol or cholesterol analogue, and
    unbound complex is removed.

10. The method of claim 8 wherein
    the ABC transporter protein is expressed in insect cells,
    the insect cells either before or during expression of the ABC transporter protein are incubated with a complex of cyclodextrin and the cholesterol or cholesterol analogue, unbound complex is removed, and
a cell membrane preparation is prepared from the insect cells.

11. The method of claim 8 wherein
the ABC transporter protein is expressed in insect cells,
the cell membrane preparation is prepared from the insect cells, comprising at least the following steps
   i) membrane isolation,
   ii) homogenization,
   iii) incubation of the homogenized preparation with a complex of cyclodextrin and the cholesterol or cholesterol analogue, and
   iv) ultracentrifugation.

12. The method of claim 8 wherein the increased substrate transport activity of the ABC transporter protein is tested by
   a) a vesicular transport assay or
   b) a substrate stimulated ATP-ase assay.

13. The insect cell preparation or an insect cell membrane preparation according to claim 1 comprising an increased membrane cholesterol level as compared to the physiological cholesterol level present in the same type of insect cell membrane and an ABC transporter protein of increased substrate transport activity as compared to the substrate transport activity of said ABC transporter protein in an insect cell membrane having a physiological cholesterol content present in the same type of insect cell membrane, wherein said insect cell preparation or said insect cell membrane preparation is obtained by a method comprising
   providing an ABC transporter protein having substrate transport activity in an insect cell preparation or an insect cell membrane preparation,
   loading the insect cell preparation or the insect cell membrane preparation with cholesterol thereby increasing cholesterol level of the insect cell preparation or the insect cell membrane preparation,
   testing the obtained cholesterol loaded insect cell preparation or insect cell membrane preparation for increased substrate transport activity of the ABC transporter protein as compared to the same activity in a control insect cell preparation or insect cell membrane preparation of the same type with a physiological cholesterol level present in the same type of insect cell membrane
   wherein the ABC transporter protein is ABCG2 or ABCB11.

14. An assay method for studying interaction of a compound and an ABC transporter protein by assessing activity of said ABC transporter protein, wherein said assay method comprises the steps of
   providing an active ABC transporter protein in an insect cell or in an insect cell membrane preparation,
   contacting a first compound with the ABC transporter protein,
   measuring any activity of the ABC transporter protein in the presence and in the absence of said first compound,
   comparing the activity values obtained in the presence and in the absence of the first compound,
   wherein
   the insect cell preparation or the insect cell membrane preparation has an increased cholesterol level as compared to a control insect cell preparation or insect cell membrane preparation having a physiological cholesterol level present in the same type of insect cell membrane and
   wherein an insect cell preparation or an insect cell membrane preparation according to claim 1 is used, and
   the ABC transporter protein is ABCG2 or ABCB11.

15. The assay method of claim 14 further comprising testing simultaneous interaction of at least two compounds and an ABC transporter protein by assessing activity of the transporter protein, said method comprising at least the steps of
   providing an active ABC transporter protein in an insect cell or in an insect cell membrane preparation,
   contacting said first compound with the ABC transporter protein,
   measuring an activity of the ABC transporter protein in the presence and in the absence of said first compound,
   comparing the activity values obtained in the presence and in the absence of said first compound,
   contacting a second compound with the ABC transporter protein in the presence of the first compound,
   measuring the activity of the ABC transporter protein in the presence of the first and the second compound simultaneously,
   comparing the activity values obtained in the presence and in the absence of the second compound,
   evaluating the effect of the second compound to the activity in the presence of the first compound.

16. The assay method of claim 14, wherein at least one of the following is determined:
   a) substrate transport activity of the ABC transporter protein,
   b) vesicular transport of a substrate by the ABC transporter,
   c) nucleotide occlusion/trapping by the ABC transporter, or
   d) basal ATPase activity of the ABC transporter.

17. The method of claim 14 wherein the ABC transporter protein is ABCG2.

18. The assay method of claim 15, wherein at least one of the following is determined:
   a) substrate transport activity of the ABC transporter protein,
   b) vesicular transport of a substrate by the ABC transporter,
   c) nucleotide occlusion/trapping by the ABC transporter, or
   d) basal ATPase activity of the ABC transporter.

19. The assay method of claim 16, wherein the substrate transport activity of the ABC transporter protein is substrate stimulated ATP-ase activity.

20. The method of claim 8 further comprising transforming the insect cells with a vector comprising a nucleic acid encoding an ABC transporter.

21. The method of claim 14 wherein the ABC transporter protein is ABCB11.

* * * * *